US008642745B2

(12) United States Patent
Arathoon et al.

(10) Patent No.: US 8,642,745 B2
(45) Date of Patent: Feb. 4, 2014

(54) METHOD FOR MAKING MULTISPECIFIC ANTIBODIES HAVING HETEROMULTIMERIC AND COMMON COMPONENTS

(75) Inventors: W. Robert Arathoon, San Mateo, CA (US); Paul J. Carter, Seattle, WA (US); Anne M. Merchant, Redwood City, CA (US); Leonard G. Presta, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 1452 days.

(21) Appl. No.: 11/608,673

(22) Filed: Dec. 8, 2006

(65) Prior Publication Data
US 2007/0178552 A1    Aug. 2, 2007

Related U.S. Application Data

(63) Continuation of application No. 09/520,130, filed on Mar. 7, 2000, which is a continuation of application No. 09/070,416, filed on Apr. 30, 1998, now abandoned.

(60) Provisional application No. 60/050,661, filed on Jun. 24, 1997, provisional application No. 60/046,816, filed on May 2, 1997.

(51) Int. Cl.
C07K 1/22      (2006.01)
C07K 16/46     (2006.01)
C12P 21/08     (2006.01)

(52) U.S. Cl.
CPC ............... *C07K 1/22* (2013.01); *Y10S 435/972* (2013.01)
USPC ................ 530/417; 530/387.1; 530/387.3; 530/412; 530/413; 530/415; 530/416; 435/69.1; 435/69.6; 435/69.7; 435/70.1; 435/71.1; 435/972

(58) Field of Classification Search
USPC ........ 530/387.3, 387.1, 387.2, 412, 413, 415, 530/416, 417; 536/23.53; 435/328, 69.1, 435/69.6, 69.7, 70.1, 71.1, 972
See application file for complete search history.

(56) References Cited

U.S. PATENT DOCUMENTS

| 4,816,567 | A | 3/1989 | Cabilly et al. |
| 5,116,964 | A | 5/1992 | Capon et al. |
| 5,591,828 | A | 1/1997 | Bosslet et al. |
| 5,731,168 | A | 3/1998 | Carter et al. |
| 5,807,706 | A | 9/1998 | Carter et al. |
| 5,821,333 | A | 10/1998 | Carter et al. |
| 6,515,110 | B1 | 2/2003 | Whitlow et al. |
| 7,183,076 | B2 | 2/2007 | Arathoon et al. |
| 7,262,028 | B2 * | 8/2007 | Van Berkel et al. ......... 435/69.6 |
| 7,642,228 | B2 | 1/2010 | Carter et al. |
| 7,695,937 | B2 | 4/2010 | Baum |
| 8,216,805 | B2 | 7/2012 | Carter et al. |
| 2013/0089553 | A1 | 4/2013 | Carter et al. |

FOREIGN PATENT DOCUMENTS

| EP | 314317 | 5/1989 |
| WO | WO 89/02922 | 4/1989 |
| WO | WO 91/08298 | 6/1991 |
| WO | WO 92/10209 | 6/1992 |
| WO | WO 92/22653 | 12/1992 |
| WO | WO 93/06217 | 4/1993 |
| WO | WO 93/11162 | 6/1993 |
| WO | WO 96/27011 | 9/1996 |
| WO | WO 96/37621 | 11/1996 |

OTHER PUBLICATIONS

Ashkenazi et al., "Protection against endotoxic shock by a tumor necrosis factor receptor immunoadhesin", *Proc. Natl. Acad. Sci. USA*, 88:10535-10539 (1991).
Barton, "Protein sequence alignment and database scanning", *Protein Structure Prediction*, pp. 31-63 (1996).
Bedzyk et al., "Active Site Structure and Antigen Binding Properties of Idiotypically Cross-reactive Anti-fluorescein Monoclonal Antibodies", *The Journal of Biological Chemistry*, 265(1):133-138 (1990).
Berg et al., "Bispecific Antibodies that Mediate Killing of Cells Infected with Human Immunodeficiency Virus of Any Strain", *Proc. Natl. Acad. Sci. USA*, 88:4723-4727 (1991).
Berman et al., "Protection from Genital Herpes Simplex Virus Type Infection by Vaccination with Cloned Type 1 Glycoprotein D", *Science*, 227(4693):1490-1492 (1985).
Bryunck, A. et al., "Characterisation of a humanized bispecific monoclongal antibody for cancer therapy", *Br. J. Cancer*, 67:436-440 (1993).
Byrn et al., "Biological Properties of a CD4 Immunoadhesin", *Nature*, 344:667-670 (1990).
Caldas et al., *Mol. Immol.*, 39(15):941-952 (2003).
Carter et al., "Engineering Subtilisin BPN' for Site-Specific Proteolysis", *Proteins: Struct. Funct. Genet.*, 6:240-248 (1989).

(Continued)

*Primary Examiner* — Misook Yu
*Assistant Examiner* — Anne Holleran
(74) *Attorney, Agent, or Firm* — Jones Day

(57) ABSTRACT

The invention relates to a method of preparing heteromultimeric polypeptides such as bispecific antibodies, bispecific immunoadhesins and antibody-immunoadhesin chimeras. The invention also relates to the heteromultimers prepared using the method. Generally, the method provides a multispecific antibody having a common light chain associated with each heteromeric polypeptide having an antibody binding domain. Additionally the method further involves introducing into the multispecific antibody a specific and complementary interaction at the interface of a first polypeptide and the interface of a second polypeptide, so as to promote heteromultimer formation and hinder homomultimer formation; and/or a free thiol-containing residue at the interface of a first polypeptide and a corresponding free thiol-containing residue in the interface of a second polypeptide, such that a non-naturally occurring disulfide bond is formed between the first and second polypeptide. The method allows for the enhanced formation of the desired heteromultimer relative to undesired heteromultimers and homomultimers.

11 Claims, 9 Drawing Sheets

(56) References Cited

OTHER PUBLICATIONS

Carter et al., "Humanization of an anti-p!85$^{HER2}$ Antibody for Human Cancer Therapy", *Proc. Natl. Acad. Sci. USA*, 89:4285-4289 (1992).
Carter et al.,"High Level *Escherichia coli* Expression and Production of a Bivalent Humanized Antibody Fragment", *Bio/Technology*, 10:163-167 (1992).
Carter et al., "Engineering antibodies for imaging and therapy", *Curr. Opin. Biotechnology*, 8(4):449-454 (1997).
Carter et al., "Toward the Production of Bispecific Antibody Fragments for Clinical Applications", *J. Hematotherapy*, 4(5):463-470 (1995).
Chamow et al., "A Humanized,Bispecific Iramunoadhesin-Antibody That Retargets CD3+ Effectors to Kill HIV-1-Infected Cells", *Journal of Immunology*, 153:4268-4280 (1994).
Chien et al., Proc. Natl. Acad. Sci. USA, 86(14): 5532-5536 (1989).
Chothia and Lesk, "Canonical Structures for the Hypervariable Regions of Immunoglobulins", *J. Mol. Biol.*, 196(4):901-917(1987).
Clackson et al., "Making antibody fragments using phage display libraries", *Nature*, 352:624-628 (1991).
Cox et al., "A directory of human germ-line $V_x$ segments reveals a strong bias in their usage", *Eur. J. Immunol.* 24:827-836 (1994).
De Jonge et al., "Production and Characterization of Bispecific Single-Chain Antibody Fragments", *Mol. Immunol* 32(17-18)1405-1412 (1995).
de Kruif et al., "Leucine Zipper Dimerized Bivalent and Bispecific scFv Antibodies from a Semi-synthetic Antibody Phage Display Library", *Journal of Biological Chemistry*, 271(13):7630-7636 (1996).
Dietsch et al., "Bispecific Receptor Globulins, Novel Tools for the Study of Cellular Interactions", *Journal of Immunological Methods*, 162:123-132 (1993).
Ellison et al., "The nucleotide sequence of a human immunoglobulin $C_{65\ 1}$gene", *Nucleic Acids Research*, 10(13) :4071-4079 (1982).
Ellman et al., "Biosynthetic Method for Introducing Unnatural Amino Acids Site-Specifically into Proteins", *Meth. Enzvm.*, 202:301-336 (1991).
Fanger et al., "Bispecific Antibodies", *Critical Reviews in Immunology*, 12(3,4):101-124 (1992).
Feng et al., "Aligning Amino Acid Sequences: Comparison of Commonly Used Methods", *J. Mol. Evol.*, 21:112-125 (1985).
Feng et al., "Progressive Alignment and Phylogenetic Tree Construction of Protein Sequences", *Methods in Enzymology*, 183:375-387 (1990).
Feng et al., "Progressive Sequence Alignment as a Prerequisite to Correct Phylogenetic Trees", *J. Mol. Evol.*, 25:351-360 (1987).
Figini et al., "In Vitro Assembly of Repertoires of Antibody Chains on the Surface of Phage by Renaturation", *J. Mol. Biol.*, 239:68-78 (1994).
George et al., "Current Methods in Sequence Comparison and Analysis", *Macromolecular Sequencing and Synthesis*, pp. 127-149 (1988).
Giusti et al., *Proc. Natl. Acad. Sci. USA*, 84(9):2926-2930 (1987).
Goddard et al., NCBI Genbank AF048774 (1998).
Goddard et al., NCBI Genbank AF048775 (1998).
Griffiths et al., "Isolation of High Affinity Human Antibodies Directly From Large Synthetic Repertoires", *EMBO Journal*, 13:3245-3260 (1994).
Gruber et al., "Efficient Tumor Cells Lysis Mediated by a Bispecific Single Chain Antibody Expressed in *Escherichia coli* ", *Journal of Immunology*, 152:5368-5374 (1994).
Gulliver et al., "Conversion of an Anti-single-stranded DNA Active Site to an Anti-florescein Active Site through Heavy Chain Complementarity Determining Region Transplantation", *The Journal of Biological Chemistry*, 269(11):7934-7940 (1994).
Guilliver et al., "Effect of Translpantation of Antibody Heavy Chain Complementarity Determining Regions on Ligand Binding", *The Journal of Biological Chemistry*, 269(30):24040-24045 (1994).

Hammerling et al., "Use of hybrid antibody with anti-γG and anti-ferritin specificities in locating cell surface antigens by electron microscopy" *Journal of Experimental Medicine*, 128:1461-1469 (1968).
Hawkins et al., "Selection of Phage Antibodies by Binding Affinity Mimicking Affinity Maturation" *J. Mol. Biol.*, 226:889-896 (1992).
Holliger et al., "Diabodies: Small bivalent and bispecific antibody fragments", *Proc . Natl. Acad. Sci. USA*, 90:6444-6448 (1993).
Nieba et al., "Disrupting the hydrophobic patches at the antibody variable/constant domain interface: improved in vivo folding and physical characterization of an engineered scFv fragment", *Protein Engineering*, 10(4):435-444 (1997).
Nissim et al., "Antibody Fragments from a 'Single Pot' Phage Display Library as Immunochemical Reagents", *EMBO Journal*, 13(3):692-698(1994).
Nolan et al., "Bifunctional antibodies: concept, production and applications", *Biochimica et Biophysica Acta*,1040:1-11 (1990).
Pluckthun, A. et al., "New protein engineering approaches to multivalent and bispecific antibody fragments", *Immunotechnology*, 3(2):83-105 (1997).
Presta et al., "Humanization of an Antibody Directed Against IgE", *J. Immunol.*, 151(5):2623-2632 (1993).
Reddy et al., "Production of Hybrids Secreting Bispecific Antibodies Recognizing CEA and Doxorubicin", *Anticancer Research*, 13:2077-2084(1993).
Reiter et al., "Engineering interchain disulfide bonds into conserved framework regions of Fv fragments: improved biochemical characteristics of recombinant immunotoxins containing disulfide-stabilized Fv", *Protein Engineering*, 7(5):697-704 (1994).
Ridgway et al., "'Knobs-into-holes' Engineering of Antibody $C_H3$ Domains for Heavy Chain Heterodimerization", *Protein Engineering*, 9(7):617-621 (1996).
Rodrigues et al., "Engineering a humanized bispecific F(ab')$_2$ fragment for improved binding to T cells", *Int. J. Cancer*, (Suppl.) 7:45-50 (1992).
Rudikoff, "Single amino acid substitution altering antigen-binding specificity", *Immunology*, 79:1979-1983 (1982).
Segal et al., "Targeting and Activation of Cytotoxic Lymphocytes", *Chem. Immunol.*, 47:179-213 (1989).
Segal et al., "Introduction: bispecific antibodies" *J. Immunol. Methods*, 248(1-2):1-6 (2001).
Shalaby et al., "Development of Humanized Bispecific Antibodies Reactive with Cytotoxic Lymphocytes and Tumor Cells Overexpression the HER2 Protooncogene", *Journal of Experimental Medicine*, 175:217-225 (1992).
Smith et al., "Variable Region Primary Structures of Monoclonal Anti-DNA Autoantibodies from NZB/NZW $F_1$ Mice", *Molecular Immunology*, 27(5):463-470 (1990).
Sonasivilai et al., "Bispecific antibody: a tool for diagnosis and treatment of disease", *Clin. Exp. Immunol.*, 79:315-321 (1990).
Stickney et al., "Bifunctional Antibody: A Binary Radiopharmaceutical Delivery System for Imaging Colorectal Carcinoma", *Cancer Research*, 51:6650-6655 (1991).
Suresh et al., "Bispecific Monoclonal Antibodies from Hybrid Hybridomas", *Methods in Enzymology*, 121:210-228 (1986).
Tomlinson et al., "Methods for Generating Multivalent and Bispecific Antibody Fragments", *Methods Enzymol.*, 326:461-479 (2000).
Hu et al., "Minibody: A Novel Engineered Anti-Carcinoembryonic Antigen Antibody Fragment (Single-Chain Fv-$C_H3$) Which Exhibits Rapid, High-Level Targeting of Xenografts" *Cancer Research*, 56:3055-3061 (1996).
Kabat et al., *Sequences of Proteins of Immunological Interest*, 5th edition, Bethesda, MD:NIH vol. 1:688-696 (1991).
Kostelny et al., "Formation of a Bispecific Antibody by the Use of Leucine Zippers", *Journal of Immunology*, 148(5):1547-1553 (1992).
Kriangkum et al., "Bispecific and bifunctional single chain recombinant antibodies", *Biomolecular Engineering*, 18(1):31-40 (2001).
Lasky et al., "DNA Sequence Analysis of the Type-Common Glycoprotein-D Genes of Herpes Simplex Virus Types 1 and 2", *DNA*, 3(I):23-29 (1984).

(56) References Cited

OTHER PUBLICATIONS

Le Doussal et al., "Bispecif ic-Antibody-Mediated Targeting of Radiolabeled Bivalent Haptens: Theoretical, Experimental and Clinical Results", *Int. J. Cancer Sujppl.*, 7:58-62 (1992).
Le Doussal et al., "Bispecific Monoclonal Antibody-Mediated Targeting of an Indium-III-Labeled DTPA Dimer to Primary Colorectal Tumors: Pharmacokinetics, Biodistribution, Scintigraphy and Immune Response", *J. Nucl. Med.*, 34:1662-1671 (1993).
Luo et al., "V1-Linker-Vh Orientation-Dependent Expression of Single Chain Fv Containing an Engineered Disulfide-Stabilized Bond in the Framework Regions", *J. Biochem.*, 118:825-831 (1995).
Mallender et al., "Comparative Properties of the Single Chain Antibody and Fv Derivatives of mAb 4-4-20", *The Journal of Biological Chemistry*, 271(10):5338-5364 (1996).
Mallender et al., "Construction, Expression, and Activity of a Bivalent Bispecific Single-chain Antibody", *The Journal of Biological Chemistry*, 269(1):199-206 (1994).
Mariuzza et al., *Annu. Rev. Biophys. Biophys. Chem.*, 16:139-59 (1987).
Marks et al., "By-Passing Immunization: Building High Affinity Human Antibodies by Chain Shuffling", *Bio/Technology*, 10:779-783 (1992).
Marks et al., "By-Passing Immunization: Human Antibodies from V-Gene Libraries Displayed on Phage", *J. Mol. Biol.*, 222:581-597 (1991).
Massino et al., "Quantitative analysis of the products of IgG chain recombination in hybrid hybridomas based on affinity chromatography and radioimmunoassay", *Journal of Immunological Methods*, 201:57-66 (1997).
McCafferty et al., "Phage Antibodies: Filamentous Phage Displaying Antibody Variable Domains", *Nature*, 348:552-554 (1990).
Merchant et al., "An efficient route to human bispecific IgG", *Nature Biotechnology*, 16:677-681 (1998).
Muller et al., "A dimeric bispecific miniantibody combines two specificities with avidity", *FEBS Letter*, 432(1-2):45-49 (1998).
Muller et al., "The first Constant domain ($C_H1$ and $C_L$) of an antibody used as heterodimerization domain for bispecific miniantibodies", *FEBS Letter*, 422(2):259-264 (1998).
Tomlinson et al., "The structural repertoire of the human $V_x$ domain", *EMBO Journal*, 14(18):4628-4638 (1995).
Tso et al., "Preparation of a Bispecific F(ab')2 Targeted to the Human IL-2 Receptor", *J. Hematotherapy*, 4(5):389-394 (1995).
Vaughan et al., "Human Antibodies With Sub-nanomolar Affinities Isolated From a Large Non-immunized Phage Display Library", *Nature Biotechnology*, 14:309-314 (1996).
Vuillez et al., "Two-Step Immunoscintigraphy for Non-Small-Cell Lung Cancer Staging Using a Bispecific Anti-CEA/Anti-Indium-DTPA Antibody and an Indium-111-Labeled DTPA Dimer", *The Journal of Nuclear Medicine*, 38(4):507-511 (1997).
Waterhouse et al., "Combinatorial infection and in vivo recombination: a strategy for making large phage antibody repertoires", *Nucleic Acids Research*, 21:2665-2266 (1993).
Weiner et al., "A Human Tumor Xenograft Model of Therapy with a Bispecific Monoclonal Antibody Targeting c-erB-2 CD16", *Cancer Research*, 53:94-100 (1993).
Wells and Powers, "In vivo formation and stability of engineered disulfide bonds in subtilisin", *J. Biol. Chemistry*, 261(14):6564-6570 (1986).
Williams et al., "Cloning and sequencing of human immunoglobulin Vλ gene segments", *Eur. J. Immunol.*, 23:1456-1461.
Zhu et al., "Remodeling domain interfaces to enhance heterodimer formation", *Protein Science*, 6(4):781-788 (1997).
de Kruif et al., "Selection and Application of Human Single Chain Fv Antibody Fragments from a Semi-synthetic Phage Antibody Display Library with Designed CDR3 Regions", *J. Mol. Biol.*, 248:97-105 (1995).
Eck et al., "Gene-Based Therapy", *In: The Pharmacological Basis of Therapeutics*, Goodman and Gilman, Ed.s, Chap. 5, pp. 77-101 (1996).
Houdebine et al., "Production of pharmaceutical proteins from transgenic animals", *Journal of Biotechnology*, 34:269-287 (1994).
Verma et al., "Gene therapy—promises, problems and prospects", *Nature*, 389-239-242 (1997).
Queen, Cary et al., "A Humanized Antibody that Binds to the Interleukin 2 Receptor", Proc. Natl. Acad. Sci., vol. 86, pp. 10029-10033, (Dec. 1989).
Milstein, C., et al., "Hybrid Hybridomas and Their Use in Immunohistochemistry", Nature, vol. 305, pp. 537-540, (Oct. 1983).
Tachibana, H. et al., "Human Bifunctional Antibody Generated by Heterologous Association of Heavy and Light Chains", Hum. Antibod. Hybridomas, vol. 4, pp. 42-46, (Apr. 1993).
Tachibana, H., et al., "Increased Antigen Binding Strengths of Hybrid Antibodies Produced by Human Hybrid Hybridomas", Cytotechnology, vol. 7, pp. 1-6, (1991).
Chamow et al., *Trends Biotechnol.*, 14(2):52-60 (1996).
Favaro et al., *Current Opinion Mol. Ther*. 9(5):477-482 (2007) (abstract only).
Greenwood et al., *J. Ther. Inununol.* 1(5):247-255 (1994).
Rubanyi et al., *Molecular Aspects of Medicine* 22: 113-142 (2001).

* cited by examiner

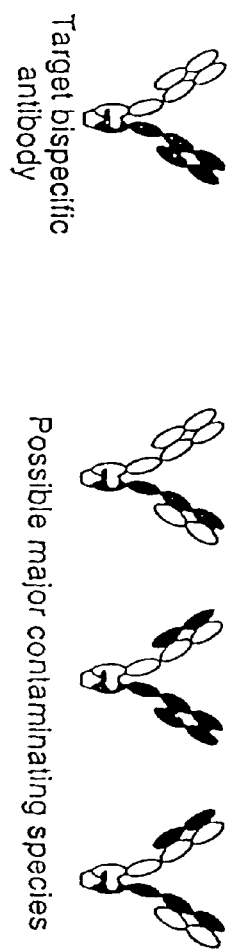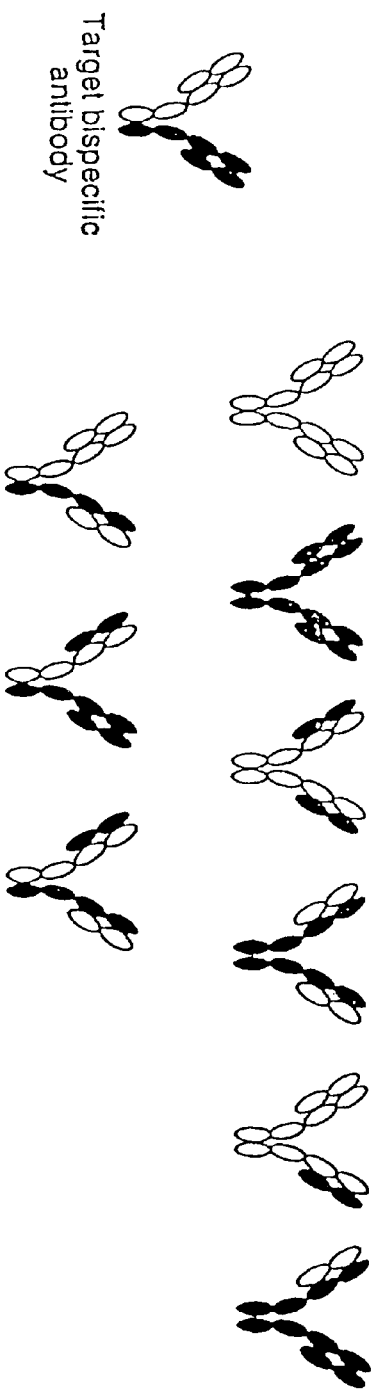

Target bispecific
antibody

Fig. 2A
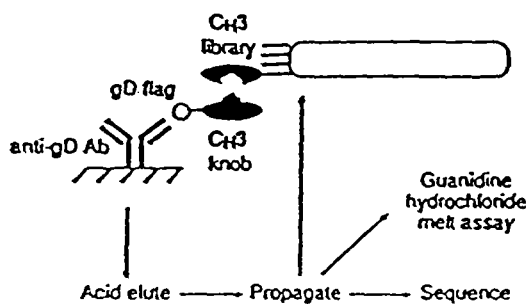
Fig. 2B
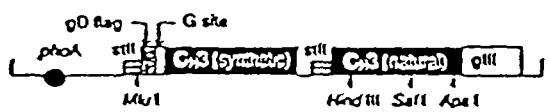
Fig. 2C
(SEQ ID NO: 13)

```
                  1              20        abc  30            40          50
Axl.78            QSVLTQPASVSGSPGQSITISCTGTSSDVGGYNYVSWYQQHPGKAPKLMIYEGSKRPSGV
Rse.23            QSVLTQPASVSGSPGQSITISCTGTSSDVGGYNYVSWYQQHPGKAPKLMIYEGSKRPSGV
IgER.MAT2C1G11    QSVLTQPASVSGSPGQSITISCTGTSSDVGGYNYVSWYQQHPGKAPKLMIYEGSKRPSGV
GCSFR.A4          QSVLTQPASVSGSPGQSITISCTGTSSDVGGYNYVSWYQQHPGKAPKLMIYEGSKRPSGV
Rse.04            QSVLTQPASVSGSPGQSITISCTGTSSDVGGYNYVSWYQQHPGKAPKLMIYEGSKRPSGV
obr.4             QSVLTQPASVSGSPGQSITISCTGTSSDVGGYNYVSWYQQHPGKAPKLMIYEGSKRPSGV
Rse.20            QSVLTQPASVSGSPGQSITISCTGTSSDVGGYNYVSWYQQHPGKGPKLMIYEGSKRPSGV
Rse.15            QSVLTQPASVSGSPGQSITISCTGTSSDVGGYNYVSWYQQHPGKGPKLMIYEGSKRPSGV
vegf.5            QSVLTQPASVSGSPGQSITISCTGTSSDVGGYNYVSWYQQHPGKAPKLMIYEGSKRPSGV
                                              ##########                  ###
                                                  CDR L1                 CDR L2

60        70        80        90    a  100
Axl.78            SNRFSGSKSGNTASLTISGLQAEDEADYYCSSYTTRSTRVFGGGTKLTVL   (SEQ ID NO: 14)
Rse.23            SNRFSGSKSGNTASLTISGLQAEDEADYYCSSYTTRSTRVFGGGTKLTVL   (SEQ ID NO: 15)
IgER.MAT2C1G11    SNRFSGSKSGNTASLTISGLQAEDEADYYCSSYTTRSTRVFGGGTKLTVL   (SEQ ID NO: 16)
GCSFR.A4          SNRFSGSKSGNTASLTISGLQAEDEADYYCSSYTTRSTRVFGGGTKLTVL   (SEQ ID NO: 17)
Rse.04            SNRFSGSKSGNTASLTISGLQAEDEADYYCSSYTTRSTRVFGGGTKLTVL   (SEQ ID NO: 18)
obr.4             SNRFSGSKSGSTASLTISGLQAEDEADYYCSSYTTRSTRVFGGGTKLTVL   (SEQ ID NO: 19)
Rse.20            SNRFSGSKXGNTASLTISGLQAEDEADYYCSSYTTRSTRVFGGGTKLTVL   (SEQ ID NO: 20)
Rse.15            SNRFSGSKSGNTASLTISGLQAEDEADYYCSSYTTRSTRVFGGGTKLTVL   (SEQ ID NO: 21)
vegf.5            SNRFSGSKSGNTASLTISGLQAEDEADYYCSSYTTRSTRVFGGGTKLTVL   (SEQ ID NO: 22)
                                                ########
                                                 CDR L3
```

```
her3.18   10        20        30   ab   40        50   a
          QVQLVQSGGGLVQPGGSLRLSCAASGFTFSSYEMN--WVRQAPGKGLEWVSGISGSGGSTYY
          ****  ** ***  *    *   *   **       * ** *******   *   *****
          EVQLVESGPGLVKPSQTLSLTCTVSGGSISSGGYYWSWIRQHPGKGLEWIGYIY-YSGSTYY
obr.26                         CDR H1                   CDR H2
```

```
    60        70        80   abc      90       100abcde      110
          ADSVKGRFTISRDNSKNTLYLQMNRLRAEDTAVYYCARDNGWELTDWYFDLWGRGTMVTVSS      (SEQ ID NO: 23)
          *  *  ***  ***   *        *  ********        *  **  ** *****
          NPSLKSRVTISVDTSKNQFSLKLSSVTAADTAVYYCARVDLEDYGSGASDYWGQGTLVTVSS      (SEQ ID NO: 24)
          CDR H2                                CDR H3
```

V_L

```
her3.18    10        20        30        40         50         60
           DIQMTQSPSTLSASIGDRVTITCRASEGIYHWLAWYQQKPGKAPKLLIYKASSLASGAPSRF
obr.26                            CDR L1                  CDR L2
```

```
           70        80        90         100
           SGSGSGTDFTLTISSLQPDDFATYYCQQYSNYPLTFGGGTKLEIK      (SEQ ID NO: 25)
                                    CDR L3
```

Fig. 5

Percentage Identity of anti-ObR and anti-HER3 $V_L$

|     | H1 | H2  | H3 | H4 | H5 | H6  | H7 | H8 | H9  | H10 | H11 |
|-----|----|-----|----|----|----|-----|----|----|-----|-----|-----|
| O1  | 49 | 47  | 51 | 81 | 60 | 48  | 76 | 51 | 100 | 62  | 51  |
| O2  | 84 | 79  | 88 | 50 | 48 | 99  | 48 | 88 | 48  | 45  | 88  |
| O3  | 83 | 82  | 85 | 51 | 50 | 95  | 49 | 85 | 49  | 46  | 85  |
| O4  | 47 | 50  | 51 | 83 | 77 | 48  | 65 | 51 | 73  | 64  | 51  |
| O5  | 49 | 47  | 51 | 81 | 60 | 48  | 76 | 51 | 100 | 62  | 51  |
| O6  | 83 | 79  | 86 | 50 | 50 | 99  | 47 | 86 | 48  | 45  | 86  |
| O7  | 81 | 100 | 86 | 51 | 49 | 80  | 48 | 86 | 47  | 44  | 86  |
| O8  | 81 | 100 | 86 | 51 | 49 | 80  | 48 | 86 | 47  | 44  | 86  |
| O9  | 81 | 100 | 86 | 51 | 49 | 80  | 48 | 86 | 47  | 44  | 86  |
| O10 | 83 | 79  | 85 | 50 | 49 | 98  | 46 | 85 | 48  | 45  | 85  |
| O11 | 83 | 80  | 87 | 50 | 49 | 99  | 47 | 87 | 48  | 45  | 87  |
| O12 | 81 | 100 | 86 | 51 | 49 | 80  | 48 | 86 | 47  | 44  | 86  |
| O13 | 49 | 47  | 51 | 81 | 60 | 48  | 76 | 51 | 100 | 62  | 51  |
| O14 | 50 | 50  | 54 | 95 | 67 | 49  | 76 | 54 | 75  | 62  | 54  |
| O15 | 82 | 79  | 85 | 49 | 48 | 97  | 46 | 85 | 47  | 44  | 85  |
| O16 | 84 | 80  | 87 | 50 | 49 | 100 | 47 | 87 | 48  | 45  | 87  |
| O17 | 45 | 44  | 47 | 65 | 62 | 45  | 62 | 47 | 62  | 100 | 47  |
| O18 | 50 | 51  | 50 | 75 | 79 | 50  | 63 | 50 | 66  | 62  | 50  |

O1-O18: Anti-Ob-R antibody clones obr. 1, 11, 12, 14, 15, 16, 17, 18, 19, 2, 20, 21, 22, 23, 24, 26, 3, 4, respectively.

H1-H11: Anti-HER3 antibody clones her3.1, 3.10, 3.11, 3.12, 3.16, 3.18, 3.19, 3.22, 3.3, 3.4, 3.7, respectively.

Fig. 8

```
                         SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
             (A) LENGTH: 36 base pairs
             (B) TYPE: Nucleic Acid
             (C) STRANDEDNESS: Single
             (D) TOPOLOGY: Linear (xi) SEQUENCE DESCRIPTION: SEQ ID NO: 1:

CTCTTCCCGA GATGGGGGCA GGGTGCACAC CTGTGG                                36

(2) INFORMATION FOR SEQ ID NO: 2:

(i) SEQUENCE CHARACTERISTICS:
             (A) LENGTH: 21 base pairs
             (B) TYPE: Nucleic Acid
             (C) STRANDEDNESS: Single
             (D) TOPOLOGY: Linear (xi) SEQUENCE DESCRIPTION: SEQ ID NO: 2:

CTCTTCCCGA CATGGGGGCA G                                                21

(2) INFORMATION FOR SEQ ID NO: 3:

(i) SEQUENCE CHARACTERISTICS:
             (A) LENGTH: 21 base pairs
             (B) TYPE: Nucleic Acid
             (C) STRANDEDNESS: Single
             (D) TOPOLOGY: Linear (xi) SEQUENCE DESCRIPTION: SEQ ID NO: 3:

GGTCATCTCA CACCGGGATG G                                                21

(2) INFORMATION FOR SEQ ID NO: 4:

(i) SEQUENCE CHARACTERISTICS:
             (A) LENGTH: 24 base pairs
             (B) TYPE: Nucleic Acid
             (C) STRANDEDNESS: Single
             (D) TOPOLOGY: Linear (xi) SEQUENCE DESCRIPTION: SEQ ID NO: 4:

CTTGGTCATA CATTCACGGG ATGG                                             24

(2) INFORMATION FOR SEQ ID NO: 5:

(i) SEQUENCE CHARACTERISTICS:
             (A) LENGTH: 30 base pairs
             (B) TYPE: Nucleic Acid
             (C) STRANDEDNESS: Single
             (D) TOPOLOGY: Linear (xi) SEQUENCE DESCRIPTION: SEQ ID NO: 5:
```

```
CTCTTCCCGA GATGGGGGAC AGGTGTACAC                                      30

(2) INFORMATION FOR SEQ ID NO: 6:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 6:

GCCGTCGGAA CACAGCACGG G                                               21

(2) INFORMATION FOR SEQ ID NO: 7:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO: 7:

CTGGGAGTCT AGAACGGGAG GCGTGGTACA GTAGTTGTT                             39

(2) INFORMATION FOR SEQ ID NO: 8:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO: 8:

GTCGGAGTCT AGAACGGGAG GACAGGTCTT GTA                                  33

(2) INFORMATION FOR SEQ ID NO: 9:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 9:

GTCGGAGTCT AGACAGGGAG G                                               21

(2) INFORMATION FOR SEQ ID NO: 10:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 10:

GCCGTCGGAG CTCAGCACGG G                                               21

(2) INFORMATION FOR SEQ ID NO: 11:

(i) SEQUENCE CHARACTERISTICS:
        (A) LENGTH: 24 base pairs
        (B) TYPE: Nucleic Acid
        (C) STRANDEDNESS: Single
        (D) TOPOLOGY: Linear (xi) SEQUENCE DESCRIPTION: SEQ ID NO: 11:

GGGAGGCGTG GTGCTGTAGT TGTT                                            24
```

(2) INFORMATION FOR SEQ ID NO: 12:

(i) SEQUENCE CHARACTERISTICS:
        (A) LENGTH: 38 base pairs
        (B) TYPE: Nucleic Acid
        (C) STRANDEDNESS: Single
        (D) TOPOLOGY: Linear (xi) SEQUENCE DESCRIPTION: SEQ ID NO: 12:

```
GTTCAGGTGC TGGGCTCGGT GGGCTTGTGT GAGTTTTG                       38
```

(2) INFORMATION FOR SEQ ID NO: 13:

(i) SEQUENCE CHARACTERISTICS:
        (A) LENGTH: 821 base pairs
        (B) TYPE: Nucleic Acid
        (C) STRANDEDNESS: Single
        (D) TOPOLOGY: Linear (xi) SEQUENCE DESCRIPTION: SEQ ID NO: 13:

```
AACGCGTACG CTCTGAAAAT GGCGGACCCG AACCGTTTTC GTGGTAAAGA          50
TCTGGCTGCA CACTACGGCC AGCCGCGGGA ACCTCAGGTG TATACCCTGC         100
CACCGTCTCG AGAAGAAATG ACTAAAAACC AGGTCTCTCT GTGGTGCCTG         150
GTCAAAGGTT TCTATCCGAG CGATATCGCC GTGGAATGGG AAAGCAACGG         200
TCAACCGGAA AACAACTACA AAACCACTCC ACCGGTGCTG GATTCTGATG         250
GCTCCTTCTT TCTGTATTCG AAGCTGACCG TTGACAAAAG CCGTTGGCAG         300
CAAGGCAACG TTTTCAGCTG TTCTGTTATG CACGAGGCCT TGCACAACCA         350
CTACACCCAG AAAAGCCTGT CCCTGTCTCC CGGGAAATAA GCTGAGGCTC         400
CTCTAGAGGT TGAGGTGATT TTATGAAAAA GAATATCGCA TTTCTTCTTG         450
CATCTATGTT CGTTTTTTCT ATTGCTACAA ACGCGTACGC TGGGCAGCCC         500
CGAGAACCAC AGGTGTACAC CCTGCCCCCA TCCCGGGAAG AGATGACCAA         550
GAACCAGGTA AGCTTGTACT GCCTGGTCAA AGGCTTCTAT CCCAGCGACA         600
TCGCCGTGGA GTGGGAGAGC AATGGGCAGC CGGAGAACAA CTACAAGACC         650
ACGCCTCCCG TGCTGGACTC CGACGGCTCC TTCTTCCTCT ACAGCTTTCT         700
CACCGTCGAC AAGAGCAGGT GGCAGCAGGG GAACGTCTTC TCATGCTCCG         750
TGATGCATGA GGCTCTGCAC AACCACTACA CGCAGAAGAG CCTCTCCCTG         800
TCTCCGGGTA AATAGGGGCC C                                        821
```

(2) INFORMATION FOR SEQ ID NO: 14:

(i) SEQUENCE CHARACTERISTICS:
        (A) LENGTH: 50 amino acids
        (B) TYPE: Amino Acid
        (D) TOPOLOGY: Linear (xi) SEQUENCE DESCRIPTION: SEQ ID NO: 14:

```
Ser Asn Arg Phe Ser Gly Ser Lys Ser Gly Asn Thr Ala Ser Leu
 1               5                  10                  15

Thr Ile Ser Gly Leu Gln Ala Glu Asp Glu Ala Asp Tyr Tyr Cys
                20                  25                  30

Ser Ser Tyr Thr Thr Arg Ser Thr Arg Val Phe Gly Gly Gly Thr
                35                  40                  45

Lys Leu Thr Val Leu
                50
```

(2) INFORMATION FOR SEQ ID NO: 15:

(i) SEQUENCE CHARACTERISTICS:
        (A) LENGTH: 50 amino acids
        (B) TYPE: Amino Acid
        (D) TOPOLOGY: Linear (xi) SEQUENCE DESCRIPTION: SEQ ID NO: 15:

```
Ser Asn Arg Phe Ser Gly Ser Lys Ser Gly Asn Thr Ala Ser Leu
 1               5                  10                  15

Thr Ile Ser Gly Leu Gln Ala Glu Asp Glu Ala Asp Tyr Tyr Cys
            20                  25                  30

Ser Ser Tyr Thr Thr Arg Ser Thr Arg Val Phe Gly Gly Gly Thr
            35                  40                  45

Lys Leu Thr Val Leu
            50
```

(2) INFORMATION FOR SEQ ID NO: 16:

(i) SEQUENCE CHARACTERISTICS:
        (A) LENGTH: 50 amino acids
        (B) TYPE: Amino Acid
        (D) TOPOLOGY: Linear (xi) SEQUENCE DESCRIPTION: SEQ ID NO: 16:

```
Ser Asn Arg Phe Ser Gly Ser Lys Ser Gly Asn Thr Ala Ser Leu
 1               5                  10                  15

Thr Ile Ser Gly Leu Gln Ala Glu Asp Glu Ala Asp Tyr Tyr Cys
            20                  25                  30

Ser Ser Tyr Thr Thr Arg Ser Thr Arg Val Phe Gly Gly Gly Thr
            35                  40                  45

Lys Leu Thr Val Leu
            50
```

(2) INFORMATION FOR SEQ ID NO: 17:

(i) SEQUENCE CHARACTERISTICS:
        (A) LENGTH: 50 amino acids
        (B) TYPE: Amino Acid
        (D) TOPOLOGY: Linear (xi) SEQUENCE DESCRIPTION: SEQ ID NO: 17:

```
Ser Asn Arg Phe Ser Gly Ser Lys Ser Gly Asn Thr Ala Ser Leu
 1               5                  10                  15

Thr Ile Ser Gly Leu Gln Ala Glu Asp Glu Ala Asp Tyr Tyr Cys
            20                  25                  30

Ser Ser Tyr Thr Thr Arg Ser Thr Arg Val Phe Gly Gly Gly Thr
            35                  40                  45

Lys Leu Thr Val Leu
            50
```

(2) INFORMATION FOR SEQ ID NO: 18:

(i) SEQUENCE CHARACTERISTICS:
        (A) LENGTH: 50 amino acids
        (B) TYPE: Amino Acid
        (D) TOPOLOGY: Linear (xi) SEQUENCE DESCRIPTION: SEQ ID NO: 18:

```
Ser Asn Arg Phe Ser Gly Ser Lys Ser Gly Asn Thr Ala Ser Leu
 1               5                  10                  15
```

```
Thr Ile Ser Gly Leu Gln Ala Glu Asp Glu Ala Asp Tyr Tyr Cys
                20                  25                  30

Ser Ser Tyr Thr Thr Arg Ser Thr Arg Val Phe Gly Gly Gly Thr
            35                  40                  45

Lys Leu Thr Val Leu
            50

(2) INFORMATION FOR SEQ ID NO: 19:

(i) SEQUENCE CHARACTERISTICS:
        (A) LENGTH: 50 amino acids
        (B) TYPE: Amino Acid
        (D) TOPOLOGY: Linear (xi) SEQUENCE DESCRIPTION: SEQ ID NO: 19:

Ser Asn Arg Phe Ser Gly Ser Lys Ser Gly Ser Thr Ala Ser Leu
1               5                   10                  15

Thr Ile Ser Gly Leu Gln Ala Glu Asp Glu Ala Asp Tyr Tyr Cys
                20                  25                  30

Ser Ser Tyr Thr Thr Arg Ser Thr Arg Val Phe Gly Gly Gly Thr
            35                  40                  45

Lys Leu Thr Val Leu
            50

(2) INFORMATION FOR SEQ ID NO: 20:

(i) SEQUENCE CHARACTERISTICS:
        (A) LENGTH: 50 amino acids
        (B) TYPE: Amino Acid
        (D) TOPOLOGY: Linear (xi) SEQUENCE DESCRIPTION: SEQ ID NO: 20:

Ser Asn Arg Phe Ser Gly Ser Lys Xaa Gly Asn Thr Ala Ser Leu
1               5                   10                  15

Thr Ile Ser Gly Leu Gln Ala Glu Asp Glu Ala Asp Tyr Tyr Cys
                20                  25                  30

Ser Ser Tyr Thr Thr Arg Ser Thr Arg Val Phe Gly Gly Gly Thr
            35                  40                  45

Lys Leu Thr Val Leu
            50

(2) INFORMATION FOR SEQ ID NO: 21:

(i) SEQUENCE CHARACTERISTICS:
        (A) LENGTH: 50 amino acids
        (B) TYPE: Amino Acid
        (D) TOPOLOGY: Linear (xi) SEQUENCE DESCRIPTION: SEQ ID NO: 21:

Ser Asn Arg Phe Ser Gly Ser Lys Ser Gly Asn Thr Ala Ser Leu
1               5                   10                  15

Thr Ile Ser Gly Leu Gln Ala Glu Asp Glu Ala Asp Tyr Tyr Cys
                20                  25                  30

Ser Ser Tyr Thr Thr Arg Ser Thr Arg Val Phe Gly Gly Gly Thr
            35                  40                  45

Lys Leu Thr Val Leu
            50

(2) INFORMATION FOR SEQ ID NO: 22:

(i) SEQUENCE CHARACTERISTICS:
        (A) LENGTH: 50 amino acids
```

(B) TYPE: Amino Acid
        (D) TOPOLOGY: Linear (xi) SEQUENCE DESCRIPTION: SEQ ID NO: 22:

Ser Asn Arg Phe Ser Gly Ser Lys Ser Gly Asn Thr Ala Ser Leu
1               5                   10                  15

Thr Ile Ser Gly Leu Gln Ala Glu Asp Glu Ala Asp Tyr Tyr Cys
                20                  25                  30

Ser Ser Tyr Thr Thr Arg Ser Thr Arg Val Phe Gly Gly Gly Thr
                35                  40                  45

Lys Leu Thr Val Leu
                50

(2) INFORMATION FOR SEQ ID NO: 23:

(i) SEQUENCE CHARACTERISTICS:
        (A) LENGTH: 62 amino acids
        (B) TYPE: Amino Acid
        (D) TOPOLOGY: Linear (xi) SEQUENCE DESCRIPTION: SEQ ID NO: 23:

Ala Asp Ser Val Lys Gly Arg Phe Thr Ile Ser Arg Asp Asn Ser
1               5                   10                  15

Lys Asn Thr Leu Tyr Leu Gln Met Asn Arg Leu Arg Ala Glu Asp
                20                  25                  30

Thr Ala Val Tyr Tyr Cys Ala Arg Asp Asn Gly Trp Glu Leu Thr
                35                  40                  45

Asp Trp Tyr Phe Asp Leu Trp Gly Arg Gly Thr Met Val Thr Val
                50                  55                  60

Ser Ser
    62

(2) INFORMATION FOR SEQ ID NO: 24:

(i) SEQUENCE CHARACTERISTICS:
        (A) LENGTH: 62 amino acids
        (B) TYPE: Amino Acid
        (D) TOPOLOGY: Linear (xi) SEQUENCE DESCRIPTION: SEQ ID NO: 24:

Asn Pro Ser Leu Lys Ser Arg Val Thr Ile Ser Val Asp Thr Ser
1               5                   10                  15

Lys Asn Gln Phe Ser Leu Lys Leu Ser Ser Val Thr Ala Ala Asp
                20                  25                  30

Thr Ala Val Tyr Tyr Cys Ala Arg Val Asp Leu Glu Asp Tyr Gly
                35                  40                  45

Ser Gly Ala Ser Asp Tyr Trp Gly Gln Gly Thr Leu Val Thr Val
                50                  55                  60

Ser Ser
    62

(2) INFORMATION FOR SEQ ID NO: 25:

(i) SEQUENCE CHARACTERISTICS:
        (A) LENGTH: 107 amino acids
        (B) TYPE: Amino Acid
        (D) TOPOLOGY: Linear (xi) SEQUENCE DESCRIPTION: SEQ ID NO: 25:

Asp Ile Gln Met Thr Gln Ser Pro Ser Thr Leu Ser Ala Ser Ile
1               5                   10                  15

```
Gly Asp Arg Val Thr Ile Thr Cys Arg Ala Ser Glu Gly Ile Tyr
            20                  25                  30

His Trp Leu Ala Trp Tyr Gln Gln Lys Pro Gly Lys Ala Pro Lys
            35                  40                  45

Leu Leu Ile Tyr Lys Ala Ser Ser Leu Ala Ser Gly Ala Pro Ser
            50                  55                  60

Arg Phe Ser Gly Ser Gly Ser Gly Thr Asp Phe Thr Leu Thr Ile
            65                  70                  75

Ser Ser Leu Gln Pro Asp Asp Phe Ala Thr Tyr Tyr Cys Gln Gln
            80                  85                  90

Tyr Ser Asn Tyr Pro Leu Thr Phe Gly Gly Gly Thr Lys Leu Glu
            95                 100                 105

Ile Lys
    107

(2) INFORMATION FOR SEQ ID NO: 26:

(i) SEQUENCE CHARACTERISTICS:
        (A) LENGTH: 261 amino acids
        (B) TYPE: Amino Acid
        (D) TOPOLOGY: Linear (xi) SEQUENCE DESCRIPTION: SEQ ID NO: 26:

Asn Ala Tyr Ala Leu Lys Met Ala Asp Pro Asn Arg Phe Arg Gly
 1                   5                  10                  15

Lys Asp Leu Ala Ala His Tyr Gly Gln Pro Arg Glu Pro Gln Val
            20                  25                  30

Tyr Thr Leu Pro Pro Ser Arg Glu Glu Met Thr Lys Asn Gln Val
            35                  40                  45

Ser Leu Trp Cys Leu Val Lys Gly Phe Tyr Pro Ser Asp Ile Ala
            50                  55                  60

Val Glu Trp Glu Ser Asn Gly Gln Pro Glu Asn Asn Tyr Lys Thr
            65                  70                  75

Thr Pro Pro Val Leu Asp Ser Asp Gly Ser Phe Phe Leu Tyr Ser
            80                  85                  90

Lys Leu Thr Val Asp Lys Ser Arg Trp Gln Gln Gly Asn Val Phe
            95                 100                 105

Ser Cys Ser Val Met His Glu Ala Leu His Asn His Tyr Thr Gln
           110                 115                 120

Lys Ser Leu Ser Leu Ser Pro Gly Lys Xaa Met Lys Lys Asn Ile
           125                 130                 135

Ala Phe Leu Leu Ala Ser Met Phe Val Phe Ser Ile Ala Thr Asn
           140                 145                 150

Ala Tyr Ala Gly Gln Pro Arg Glu Pro Gln Val Tyr Thr Leu Pro
           155                 160                 165

Pro Ser Arg Glu Glu Met Thr Lys Asn Gln Val Ser Leu Tyr Cys
           170                 175                 180

Leu Val Lys Gly Phe Tyr Pro Ser Asp Ile Ala Val Glu Trp Glu
           185                 190                 195

Ser Asn Gly Gln Pro Glu Asn Asn Tyr Lys Thr Thr Pro Pro Val
           200                 205                 210

Leu Asp Ser Asp Gly Ser Phe Phe Leu Tyr Ser Phe Leu Thr Val
           215                 220                 225

Asp Lys Ser Arg Trp Gln Gln Gly Asn Val Phe Ser Cys Ser Val
           230                 235                 240

Met His Glu Ala Leu His Asn His Tyr Thr Gln Lys Ser Leu Ser
```

Leu Ser Pro Gly Lys Xaa
           260 261

(2) INFORMATION FOR SEQ ID NO: 27:

(i) SEQUENCE CHARACTERISTICS:
        (A) LENGTH: 717 base pairs
        (B) TYPE: Nucleic Acid
        (C) STRANDEDNESS: Single
        (D) TOPOLOGY: Linear (xi) SEQUENCE DESCRIPTION: SEQ ID NO: 27:

```
CAGGTGCAGC TGGTGCAGTC TGGGGGAGGC TTGGTCCGGC CCGGGGGGTC          50

CCTGAGTCTC TCCTGTGCAG TCTCTGGAAT CACCCTCAGG ACCTACGGCA         100

TGCACTGGGT CCGCCAGGCT CCAGGCAAGG GGCTGGAGTG GGTGGCAGGT         150

ATATCCTTTG ACGGAAGAAG TGAATACTAT GCAGACTCCG TGCAGGGCCG         200

ATTCACCATC TCCAGAGACA GTTCCAAGAA CACCCTGTAT CTGCAAATGA         250

ACAGCCTGAG AGCCGAGGAC ACGGCTGTGT ATTACTGTGC GAGAGGAGCA         300

CATTATGGTT TCGATATCTG GGGCCAAGGG ACAATGGTCA CCGTCTCGAG         350

TGGTGGAGGC GGTACAGGCG GAGGTGGCAG CGGCGGTGGC GGATCGGACA         400

TCCAGATGAC CCAGTCTCCT TCCACCCTGT CTGCATCTAT GGAGACAGA          450

GTCACCATCA CCTGCCGGGC CAGCGAGGGT ATTTATCACT GGTTGGCCTG         500

GTATCAGCAG AAGCCAGGGA AAGCCCCTAA ACTCCTGATC TATAAGGCCT         550

CTAGTTTAGC CAGTGGGGCC CCATCAAGGT TCAGCGGCAG TGGATCTGGG         600

ACAGATTTCA CTCTCACCAT CAGCAGCCTG CAGCCTGATG ATTTTGCAAC         650

TTATTACTGC CAACAATATA GTAATTATCC GCTCACTTTC GGCGGAGGGA         700

CCAAGCTGGA GATCAAA                                             717
```

(2) INFORMATION FOR SEQ ID NO: 28:

(i) SEQUENCE CHARACTERISTICS:
        (A) LENGTH: 732 base pairs
        (B) TYPE: Nucleic Acid
        (C) STRANDEDNESS: Single
        (D) TOPOLOGY: Linear (xi) SEQUENCE DESCRIPTION: SEQ ID NO: 28:

```
CAGGTGCAGC TGGTGCAATC TGGGGGAGGC TTGGTACAGC ATGGAGGGTC          50

CCTGAGACTC TCCTGTGCAG CCTCTGGATT CACCTTCAGT AGTTATGAAA         100

TGAACTGGGT CCGCCAGGCT CCAGGGAAGG GGCTGGAGTG GGTCTCAGGT         150

ATTAGTGGTA GTGGTGGTAG CACATACTAC GCAGACTCCG TGAAGGGCCG         200

GTTCACCATC TCCAGAGACA ATTCCAAGAA CACGCTGTAT CTGCAAATGA         250

ACAGACTGAG AGCTGAGGAC ACGGCTGTGT ATTACTGTGC GAGAGATAAT         300

GGGTGGGAAC TAACGGACTG GTACTTCGAT CTCTGGGGCC GGGGGACAAT         350

GGTCACCGTC TCCTCAGGTG GAGGCGGTTC AGGCGGAGGT GGCAGCGGCG         400

GTGGCGGATC GGACATCCAG ATGACCCAGT CTCCTTCCAC CCTGTCTGCA         450

TCTATTGGAG ACAGAGTCAC CATCACCTGC CGGGCCAGTG AGGGTATTTA         500

TCACTGGTTG GCCTGGTATC AGCAGAAGCC AGGGAAAGCC CTAAACTCC          550

TGATCTATAA GGCCTCTAGT TTAGCCAGTG GGGCCCCATC AAGGTTCAGC         600
```

| | |
|---|---|
| GGCAGTGGAT CTGGGACAGA TTTCACTCTC ACCATCAGCA GCCTGCAGCC | 650 |
| TGATGATTTT GCAACTTATT ACTGCCAACA ATATAGTAAT TATCCGCTCA | 700 |
| CTTTCGGCGG AGGGACCAAG CTGGAGATCA AA | 732 |

METHOD FOR MAKING MULTISPECIFIC ANTIBODIES HAVING HETEROMULTIMERIC AND COMMON COMPONENTS

CROSS REFERENCE TO RELATED APPLICATION

This application is a continuation application of U.S. application Ser. No. 09/520,130, filed Mar. 7, 2000, which is a continuation application of U.S. application Ser. No. 09/070,416, filed Apr. 30, 1998, claiming priority under 35 USC 119(e) to provisional application No. 60/050,661, filed Jun. 24, 1997, and provisional application No. 60/046,816, filed May 2, 1997, which applications are incorporated herein by reference.

FIELD OF THE INVENTION

This invention relates to a method for making multispecific antibodies having heteromultimeric heavy chain components and common light chain components such as bispecific antibodies, bispecific immunoadhesins, as well as antibody-immunoadhesin chimeras and the heteromultimeric polypeptides made using the method.

BACKGROUND OF THE INVENTION

Bispecific Antibodies

Bispecific antibodies (BsAbs) which have binding specificities for at least two different antigens have significant potential in a wide range of clinical applications as targeting agents for in vitro and in vivo immunodiagnosis and therapy, and for diagnostic immunoassays.

In the diagnostic areas, bispecific antibodies have been very useful in probing the functional properties of cell surface molecules and in defining the ability of the different Fc receptors to mediate cytotoxicity (Fanger et al., Crit. Rev. Immunol. 12:101-124 (1992)). Nolan et al., Biochem. Biophys. Acta. 1040:1-11 (1990) describe other diagnostic applications for BsAbs. In particular, BsAbs can be constructed to immobilize enzymes for use in enzyme immunoassays. To achieve this, one arm of the BsAb can be designed to bind to a specific epitope on the enzyme so that binding does not cause enzyme inhibition, the other arm of the BsAb binds to the immobilizing matrix ensuring a high enzyme density at the desired site. Examples of such diagnostic BsAbs include the rabbit anti-IgG/anti-ferritin BsAb described by Hammerling et al., J. Exp. Med. 128:1461-1473 (1968) which was used to locate surface antigens. BsAbs having binding specificities for horse radish peroxidase (HRP) as well as a hormone have also been developed. Another potential immunochemical application for BsAbs involves their use in two-site immunoassays. For example, two BsAbs are produced binding to two separate epitopes on the analyte protein—one BsAb binds the complex to an insoluble matrix, the other binds an indicator enzyme (see Nolan et al., supra).

Bispecific antibodies can also be used for in vitro or in vivo immunodiagnosis of various diseases such as cancer (Songsivilai et al., Clin. Exp. Immunol. 79:315 (1990)). To facilitate this diagnostic use of the BsAb, one arm of the BsAb can bind a tumor associated antigen and the other arm can bind a detectable marker such as a chelator which tightly binds a radionuclide. Using this approach, Le Doussal et al. made a BsAb useful for radioimmunodetection of colorectal and thyroid carcinomas which had one arm which bound a carcinoembryonic antigen (CEA) and another arm which bound diethylenetriaminepentacetic acid (DPTA). See Le Doussal et al., Int. J. Cancer Suppl. 7:58-62 (1992) and Le Doussal et al., J. Nucl. Med. 34:1662-1671 (1993). Stickney et al. similarly describe a strategy for detecting colorectal cancers expressing CEA using radioimmunodetection. These investigators describe a BsAb which binds CEA as well as hydroxyethylthiourea-benzyl-EDTA (EOTUBE). See Stickney et al., Cancer Res. 51:6650-6655 (1991).

Bispecific antibodies can also be used for human therapy in redirected cytotoxicity by providing one arm which binds a target (e.g. pathogen or tumor cell) and another arm which binds a cytotoxic trigger molecule, such as the T-cell receptor or the Fcγ receptor. Accordingly, bispecific antibodies can be used to direct a patient's cellular immune defense mechanisms specifically to the tumor cell or infectious agent. Using this strategy, it has been demonstrated that bispecific antibodies which bind to the FcγRIII (i.e. CD16) can mediate tumor cell killing by natural killer (NK) cell/large granular lymphocyte (LGL) cells in vitro and are effective in preventing tumor growth in vivo. Segal et al., Chem. Immunol. 47:179 (1989) and Segal et al., Biologic Therapy of Cancer 2(4) DeVita et al. eds. J. B. Lippincott, Philadelphia (1992) p. 1. Similarly, a bispecific antibody having one arm which binds FcγRIII and another which binds to the HER2 receptor has been developed for therapy of ovarian and breast tumors that overexpress the HER2 antigen. (Hseih-Ma et al. Cancer Research 52:6832-6839 (1992) and Weiner et al. Cancer Research 53:94-100 (1993)). Bispecific antibodies can also mediate killing by T cells. Normally, the bispecific antibodies link the CD3 complex on T cells to a tumor-associated antigen. A fully humanized F(ab')$_2$ BsAb consisting of anti-CD3 linked to anti-p185$^{HER2}$ has been used to target T cells to kill tumor cells overexpressing the HER2 receptor. Shalaby et al., J. Exp. Med. 175(1):217 (1992). Bispecific antibodies have been tested in several early phase clinical trials with encouraging results. In one trial, 12 patients with lung, ovarian or breast cancer were treated with infusions of activated T-lymphocytes targeted with an anti-CD3/anti-tumor (MOC31) bispecific antibody. deLeij et al. *Bispecific Antibodies and Targeted Cellular Cytotoxicity*, Romet-Lemonne, Fanger and Segal Eds., Lienhart (1991) p. 249. The targeted cells induced considerable local lysis of tumor cells, a mild inflammatory reaction, but no toxic side effects or anti-mouse antibody responses. In a very preliminary trial of an anti-CD3/anti-CD19 bispecific antibody in a patient with B-cell malignancy, significant reduction in peripheral tumor cell counts was also achieved. Clark et al. Bispecific Antibodies and Targeted Cellular Cytotoxicity, Romet-Lemonne, Fanger and Segal Eds., Lienhart (1991) p. 243. See also Kroesen et al., Cancer Immunol. Immunother. 37:400-407 (1993), Kroesen et al., Br. J. Cancer 70:652-661 (1994) and Weiner et al., J. Immunol. 152:2385 (1994) concerning therapeutic applications for BsAbs.

Bispecific antibodies may also be used as fibrinolytic agents or vaccine adjuvants. Furthermore, these antibodies may be used in the treatment of infectious diseases (e.g. for targeting of effector cells to virally infected cells such as HIV or influenza virus or protozoa such as *Toxoplasma gondii*), used to deliver immunotoxins to tumor cells, or target immune complexes to cell surface receptors (see Fanger et al., supra).

Use of BsAbs has been effectively hindered by the difficulty of obtaining BsAbs in sufficient quantity and purity. Traditionally, bispecific antibodies were made using hybrid-hybridoma technology (Millstein and Cuello, Nature 305: 537-539 (1983)). Because of the random assortment of immunoglobulin heavy and light chains, these hybridomas (quadromas) produce a potential mixture of 10 different antibody molecules, of which only one has the correct bispecific structure (see FIG. 1A). The purification of the correct molecule, which is usually done by affinity chromatography steps, is rather cumbersome, and the product yields are low. See, for example, (Smith, W., et al. (1992) Hybridoma 4:87-98; and Massimo, Y. S., et al. (1997) J. Immunol. Methods 201:57-66). Accordingly, techniques for the production of greater yields of BsAb have been developed. To achieve chemical coupling of antibody fragments, Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the BsAb. The BsAbs produced can be used as agents for the selective immobilization of enzymes.

Recent progress has facilitated the direct recovery of Fab'-SH fragments from *E. coli*. which can be chemically coupled to form bispecific antibodies. Shalaby et al., J. Exp. Med. 175:217-225 (1992) describe the production of a fully humanized BsAb F(ab')$_2$ molecule having one arm which binds p185$^{HER2}$ and another arm which binds CD3. Each Fab' fragment was separately secreted from *E. coli*. and subjected to directed chemical coupling in vitro to form the BsAb. The BsAb thus formed was able to bind to cells overexpressing the HER2 receptor and normal human T cells, as well as trigger the lytic activity of human cytotoxic lymphocytes against human breast tumor targets. See also Rodrigues et al., Int. J. Cancers (Suppl.) 7:45-50 (1992).

Various techniques for making and isolating BsAb fragments directly from recombinant cell cultures have also been described. For example, bispecific F(ab')$_2$ heterodimers have been produced using leucine zippers (Kostelny et al., J. Immunol. 148(5):1547-1553 (1992)). The leucine zipper peptides from the Fos and Jun proteins were linked to the Fab' portions of anti-CD3 and anti-interleukin-2 receptor (IL-2R) antibodies by gene fusion. The antibody homodimers were reduced at the hinge region to form monomers and then reoxidized to form the antibody heterodimers. The BsAbs were found to be highly effective in recruiting cytotoxic T cells to lyse HuT-102 cells in vitro. The advent of the "diabody" technology described by Hollinger et al., PNAS (USA) 90:6444-6448 (1993) has provided an alternative mechanism for making BsAb fragments. The fragments comprise a heavy chain variable domain ($V_H$) connected to a light chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making BsAb fragments by the use of single chain Fv (sFv) dimers has also been reported. See Gruber et al. J. Immunol. 152: 5368 (1994). These researchers designed an antibody which comprised the $V_H$ and $V_L$ domains of an antibody directed against the T cell receptor joined by a 25 amino acid residue linker to the $V_H$ and $V_L$ domains of an anti-fluorescein antibody. The refolded molecule bound to fluorescein and the T cell receptor and redirected the lysis of human tumor cells that had fluorescein covalently linked to their surface.

It is apparent that several techniques for making bispecific antibody fragments which can be recovered directly from recombinant cell culture have been reported. However, full length BsAbs may be preferable to BsAb fragments for many clinical applications because of their likely longer serum half-life and possible effector functions.

Immunoadhesins

Immunoadhesins (Ia's) are antibody-like molecules which combine the binding domain of a protein such as a cell-surface receptor or a ligand (an "adhesin") with the effector functions of an immunoglobulin constant domain. Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use.

Immunoadhesins reported in the literature include fusions of the T cell receptor (Gascoigne et al., Proc. Natl. Acad. Sci. USA 84:2936-2940 (1987)); CD4 (Capon et al., Nature 337:525-531 (1989); Traunecker et al., Nature 339:68-70 (1989); Zettmeissl et al., DNA Cell Biol. USA 9:347-353 (1990); and Byrn et al., Nature 344:667-670 (1990)); L-selectin or homing receptor (Watson et al., J. Cell. Biol. 110:2221-2229 (1990); and Watson et al., Nature 349:164-167 (1991)); CD44 (Aruffo et al., Cell 61:1303-1313 (1990)); CD28 and B7 (Linsley et al., J. Exp. Med. 173:721-730 (1991)); CTLA-4 (Lisley et al., J. Exp. Med. 174:561-569 (1991)); CD22 (Stamenkovic et al., Cell 66:1133-1144 (1991)); TNF receptor (Ashkenazi et al., Proc. Natl. Acad. Sci. USA 88:10535-10539 (1991); Lesslauer et al., Eur. J. Immunol. 27:2883-2886 (1991); and Peppel et al., J. Exp. Med. 174:1483-1489 (1991)); NP receptors (Bennett et al., J. Biol. Chem. 266:23060-23067 (1991)); inteferon γ receptor (Kurschner et al., J. Biol. Chem. 267:9354-9360 (1992)); 4-1BB (Chalupny et al., PNAS (USA) 89:10360-10364 (1992)) and IgE receptor α (Ridgway and Gorman, J. Cell. Biol. Vol. 115, Abstract No. 1448 (1991)).

Examples of immunoadhesins which have been described for therapeutic use include the CD4-IgG immunoadhesin for blocking the binding of HIV to cell-surface CD4. Data obtained from Phase I clinical trials in which CD4-IgG was administered to pregnant women just before delivery suggests that this immunoadhesin may be useful in the prevention of maternal-fetal transfer of HIV. Ashkenazi et al., Intern. Rev. Immunol. 10:219-227 (1993). An immunoadhesin which binds tumor necrosis factor (TNF) has also been developed. TNF is a proinflammatory cytokine which has been shown to be a major mediator of septic shock. Based on a mouse model of septic shock, a TNF receptor immunoadhesin has shown promise as a candidate for clinical use in treating septic shock (Ashkenazi et al., supra). Immunoadhesins also have non-therapeutic uses. For example, the L-selectin receptor immunoadhesin was used as an reagent for histochemical staining of peripheral lymph node high endothelial venules (HEV). This reagent was also used to isolate and characterize the L-selectin ligand (Ashkenazi et al., supra).

If the two arms of the immunoadhesin structure have different specificities, the immunoadhesin is called a "bispecific immunoadhesin" by analogy to bispecific antibodies. Dietsch et al., J. Immunol. Methods 162:123 (1993) describe such a bispecific immunoadhesin combining the extracellular domains of the adhesion molecules, E-selectin and P-selectin.

Binding studies indicated that the bispecific immunoglobulin fusion protein so formed had an enhanced ability to bind to a myeloid cell line compared to the monospecific immunoadhesins from which it was derived.

Antibody-Immunoadhesin Chimeras

Antibody-immunoadhesin (Ab/Ia) chimeras have also been described in the literature. These molecules combine the binding region of an immunoadhesin with the binding domain of an antibody.

Berg et al., PNAS (USA) 88:4723-4727 (1991) made a bispecific antibody-immunoadhesin chimera which was derived from murine CD4-IgG. These workers constructed a tetrameric molecule having two arms. One arm was composed of CD4 fused with an antibody heavy-chain constant domain along with a CD4 fusion with an antibody light-chain constant domain. The other arm was composed of a complete heavy-chain of an anti-CD3 antibody along with a complete light-chain of the same antibody. By virtue of the CD4-IgG arm, this bispecific molecule binds to CD3 on the surface of cytotoxic T cells. The juxtaposition of the cytotoxic cells and HIV-infected cells results in specific killing of the latter cells.

While Berg et al. supra describe a bispecific molecule that was tetrameric in structure, it is possible to produce a trimeric hybrid molecule that contains only one CD4-IgG fusion. See Chamow et al., J. Immunol. 153:4268 (1994). The first arm of this construct is formed by a humanized anti-CD3 κ light chain and a humanized anti-CD3 γ heavy chain. The second arm is a CD4-IgG immunoadhesin which combines part of the extracellular domain of CD4 responsible for gp120 binding with the Fc domain of IgG. The resultant Ab/Ia chimera mediated killing of HIV-infected cells using either pure cytotoxic T cell preparations or whole peripheral blood lymphocyte (PBL) fractions that additionally included Fc receptor-bearing large granular lymphocyte effector cells.

In the manufacture of the multispecific antibody heteromultimers, it is desirable to increase the yields of the desired heteromultimer over the homomultimer(s). The current method of choice for obtaining Fc-containing BsAb remains the hybrid hybridoma, in which two antibodies are coexpressed (Milstein and Cuello, Nature 305:537-540 (1983)).

In hybrid hybridomas, heavy (H) chains typically form homodimers as well as the desired heterodimers. Additionally, light (L) chains frequently mispair with non-cognate heavy chains. Hence, coexpression of two antibodies may produce up to ten heavy and light chain pairings (Suresh, M. R., et al. Methods Enzymol. 121:210-228 (1986)). These unwanted chain pairings compromise the yield of the BsAb and inevitably impose significant, and sometimes insurmountable, purification challenges (Smith, et al. (1992) supra; and Massimo, et al. (1997) supra).

Antibody heavy chains have previously been engineered to drive heterodimerization by introducing sterically complementary mutations in multimerization domains at the $C_H3$ domain interface (Ridgway et al. Protein Eng. 9:617-621 (1996)) and optimization by phage display as described herein. Chains containing the modified $C_H3$ domains yield up to approximately 90% heterodimer as judged by formation of an antibody/immunoadhesin hybrid (Ab/Ia). Heterodimerized heavy chains may still mispair with the non-cognate light chain, thus hampering recovery of the BsAb of interest.

SUMMARY OF THE INVENTION

This application describes a strategy which serves to enhance the formation of a desired heteromultimeric bispecific antibody from a mixture of monomers by engineering an interface between a first and second polypeptide for hetero-oligomerization and by providing a common variable light chain to interact with each of the heteromeric variable heavy chain regions of the bispecific antibody. There are three possible hetero- and homomultimers that can form from a first and second polypeptide, each of which is, in turn, associated with a first and second light chain, respectively. This gives rise to a total of ten possible chain pairings (FIG. 1A). A method of enhancing the formation of the desired heteromultimer can greatly enhance the yield over undesired heteromultimers and homomultimers.

The preferred interface between a first and second polypeptide of the heteromultimeric antibody comprises at least a part of the $C_H3$ domain of an antibody constant domain. The domain of each of the first and second polypeptides that interacts at the interface is called the multimerization domain. Preferably, the multimerization domain promotes interaction between a specific first polypeptide and a second polypeptide, thereby increasing the yield of desired heteromultimer (FIG. 1B). Interaction may be promoted at the interface by the formation of protuberance-into-cavity complementary regions; the formation of non-naturally occurring disulfide bonds; leucine zipper; hydrophobic regions; and hydrophilic regions. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). Where a suitably positioned and dimensioned protuberance or cavity exists at the interface of either the first or second polypeptide, it is only necessary to engineer a corresponding cavity or protuberance, respectively, at the adjacent interface. Non-naturally occurring disulfide bonds are constructed by replacing on the first polypeptide a naturally occurring amino acid with a free thiol-containing residue, such as cysteine, such that the free thiol interacts with another free thiol-containing residue on the second polypeptide such that a disulfide bond is formed between the first and second polypeptides (FIG. 1B).

Single chain Fv fragments from a large non-immunized phage display library (Vaughan, T. J. et al. (1996) Nature Biotechnology 14:309-314, herein incorporated by reference in its entirety) revealed V-gene usage in which $V_H$ and $V_L$ sequences derived from certain germline V-gene segments predominated. families predominated in the repertoire. Examples of chain promiscuity in the repertoire were noted in which a particular heavy or light chain is found in combination with different partner chains (Vaughan, T. J. et al. (1996) supra).

It is disclosed herein that the preparation of a desired heteromultimeric multispecific antibody is enhanced when a common light chain is provided to pair with each of the variable heavy chains of the multispecific antibody. Use of a common variable light chain reduces the number of monomers that must correctly pair to form the antigen binding domains by limiting the number of light chains from two or more light chains (in a bispecific or multispecific antibody, respectively, prior to disclosure of the instant invention) to one light chain (in a multispecific antibody of the invention, see FIG. 1C).

Accordingly, the invention relates to a method of preparing a heteromultimeric multispecific antibody, the antibody comprising 1) a first polypeptide and a second polypeptide (and additional polypeptides accord to the multiplicity of the antibody) which meet at an interface, wherein the first and additional polypeptides (i.e., a first and second polypeptide) each include a multimerization domain forming an interface between the first and second (or at least one additional) polypeptides, and the multimerization domains promote stable interaction between first and additional polypeptides, and 2) a binding domain in each of the first and at least one additional polypeptide (i.e. a second polypeptide), each binding domain comprising a variable heavy chain and a variable light chain, wherein the variable light chain of the first polypeptide and the variable light chain of the second polypeptide have a common amino acid sequence, which common sequence has an amino acid sequence identity to an original light chain of each of the polypeptides of at least 80%, preferably at least 90%, more preferably at least 95% and most preferably 100% sequence identity. The method comprises the steps of (i) culturing a host cell comprising nucleic acid encoding the first polypeptide, the second polypeptide, and the common light chain wherein the culturing is such that the nucleic acid is expressed; and (ii) recovering the multispecific antibody from the host cell culture;

In a related embodiment of the invention the nucleic acid encoding the first polypeptide or the nucleic acid encoding the second polypeptide, or both, has been altered from the original nucleic acid to encode the interface or a portion thereof.

In another embodiment of the method, the interface of the first polypeptide comprises a free thiol-containing residue which is positioned to interact with a free thiol-containing residue of the interface of the second polypeptide such that a disulfide bond is formed between the first and second polypeptides. According to the invention, the nucleic acid encoding the first polypeptide has been altered from the original nucleic acid to encode the free thiol-containing residue or the nucleic acid encoding the second polypeptide has been altered from the original nucleic acid to encode the free thiol-containing residue, or both.

In another embodiment of the method, the nucleic acid encoding both the first polypeptide and at least one additional polypeptide (i.e., a second polypeptide) are altered to encode the protuberance and cavity, respectively. Preferably the first and second polypeptides each comprise an antibody constant domain such as the $C_H3$ domain of a human $IgG_1$.

In another aspect, the invention provides a heteromultimer (such as a bispecific antibody, bispecific immunoadhesin or antibody/immunoadhesin chimera) comprising a first polypeptide and a second polypeptide which meet at an interface. The interface of the first polypeptide comprises a multimerization domain which is positioned to interact with a multimerization domain on the at least one additional polypeptide (i.e., a second polypeptide) to form an interface between the first and second polypeptide. In preferred embodiments of the invention, the multimerization domains are altered to promote interaction between a specific first polypeptide and a specific second polypeptide, which alterations include, but are not limited to, the generation of a protuberance or cavity, or both; the generation of non-naturally occurring disulfide bonds; the generation of complementary hydrophobic regions; and the generation of complementary hydrophilic regions. The heteromultimeric multispecific antibody may be provided in the form of a composition further comprising a pharmaceutically acceptable carrier.

The invention also relates to a host cell comprising nucleic acid encoding the heteromultimeric multispecific antibody of the preceding paragraph wherein the nucleic acid encoding the first polypeptide and at least one additional polypeptide (i.e., a second polypeptide) is present in a single vector or in separate vectors. The host cell can be used in a method of making a heteromultimeric multispecific antibody which involves culturing the host cell so that the nucleic acid is expressed, and recovering the heteromultimeric antibody from the cell culture.

In yet a further aspect, the invention provides a method of preparing a heteromultimeric multispecific antibody comprising:

(a) selecting a first nucleic acid encoding a first polypeptide comprising an amino acid residue in the interface of the first polypeptide that is positioned to interact with an amino acid residue of interface of at least one additional polypeptide. In an embodiment the nucleic acid is altered from the original to encode the interacting amino acid residues. In another embodiment, the first nucleic acid is altered to encode an amino acid residue having a larger side chain volume, thereby generating a protuberance on the first polypeptide;

(b) altering a second nucleic acid encoding a second polypeptide so that an amino acid residue in the interface of the second polypeptide is replaced with an amino acid residue having a smaller side chain volume, thereby generating a cavity in the second polypeptide, wherein the protuberance is positioned to interact with the cavity;

(c) introducing into a host cell the first and second nucleic acids and culturing the host cell so that expression of the first and second nucleic acid occurs; and (d) recovering the heteromultimeric antibody formed from the cell culture.

It may also be desirable to construct a multispecific antibody (such as a bispecific antibody) that incorporates a previously identified antibody. Under these circumstances it is desirable to identify a heavy chain that when paired with the original light chain will bind specifically to a second antigen of interest. The methods of Figini et al. (Figini, M. et al. (1994) J. Mol. Biol. 239:68-78, herein incorporated by reference in its entirety) may be used to identify such a heavy chain. First a phage library would be treated with guanidine hydrochloride to dissociate the original light chain. Next, the heavy chains displayed on phage would be reconstituted with the light chain of interest by removing the denaturant (such as by dialysis). Panning against the second antigen of interest would then be conducted to identify the desired heavy chain. The invention further embodies a multispecific antibody prepared by this method of selecting a heavy chain to pair with a chosen light chain, nucleic acid encoding the antibody, and a host cell comprising the nucleic acid.

The invention provides a mechanism for increasing the yields of the heteromultimer over other unwanted end-products such as undesired heteromultimers and/or homomultimers (see FIG. 1A-1C). Preferably, the yields of the desired heteromultimer recovered from recombinant cell culture are at least greater than 80% by weight and preferably greater than 90% by weight compared to the by-product undesired heterodimer or homomultimer(s).

BRIEF DESCRIPTION OF THE DRAWINGS

FIGS. 1A-1C. FIG. 1A is a diagram of the formation of Fc-containing bispecific antibodies when no engineering is performed to enhance heteromultimerization over homomultimerization. FIG. 1B is a diagram showing pairing that occurs when heavy (H) chains are engineered such that desired heteromultimerization is favored over undesired heteromultimerization over homomultimerization. FIG. 1C is a diagram showing pairing that occurs when antibodies are chosen which share the same light (L) chain to circumvent the problem of light chains pairing with non-cognate heavy chains.

FIGS. 2A-2C. FIG. 2A diagrams a selection scheme for $C_H3$ heterodimer using phage display vector, pRA2. Phage displaying stable $C_H3$ heterodimers are captured using an antibody directed to the gD flag. FIG. 2B diagrams a dicistronic operon in which $C_H3$ expressed from a synthetic gene is co-secreted with a second copy of $C_H3$ expressed from the natural gene (Ellison et al. Nucleic Acids Res. 10:4071-4079 (1982)) as a fusion protein with M13 gene III protein. The synthetic $C_H3$ gene is preceded by a sequence encoding a peptide derived from herpes simplex virus glycoprotein D (gD flag, Lasky, L. A. and Dowbenko, D. J. (1984) DNA 3:23-29; Berman, P. W. et al., (1985) Science 227:1490-1492 and a cleavage (G) site for the site-specific protease, Genenase I (Carter, P. et al. (1989) Proteins: Structure, Function and Genetics 6:240-248). FIG. 2C is the nucleic acid sequence of the dicistronic operon (SEQ ID NO:1) of FIG. 2B in which the residues in the translated $C_H3$ genes are numbered according to the Eu system of Kabat et al. In Sequences of Proteins of Immunological Interest, 5th ed. vol. 1, pp. 688-696, NIH, Bethesda, Md. (1991). Protuberance mutation T366W is shown, as are the residues targeted for randomization in the natural $C_H3$ gene (366, 368, and 407).

FIGS. 3A and 3B are bar graphs of the results of scanning densitometric analysis of SDS-PAGE of protein A-purified products from cotransfection of antibody (Ab) heavy and light chains with immunoadhesin (Ia). Data presented are the mean of two independent experiments. The x-axis indicates the ratios of input DNA by mass (Ia:H:L) and the y-axis indicates the percentage of each type of product multimer with respect to total product protein. FIG. 3C is a diagram of the possible product multimers.

FIG. 4 is a comparison of the $V_L$ sequences of eight different antibodies with specificities for Axl, Rse, IgER, Ob-R, and VEGF. The position of the antigen binding CDR residues according to sequence definition (Kabat et al. (1991) supra) or structural definition (Chothia, C. and Lesk, A. M. J. Mol. Biol. (1987) 196:901-917) are shown by underlining and #, respectively. Residues that differ from the Axl.78 sequence are shown by double underlining.

FIG. 5 is a comparison of the heavy and light chains of selected anti-Ob-R and anti-HER3 clones. Shown are the $V_H$ and the common $V_L$ sequences of anti-Ob-R clone 26 and anti-HER3 clone 18 used to construct a bispecific antibody.

FIG. 8 is a matrix representing the amino acid sequence identity between the light chains of antibodies raised to HER3 versus the light chains of antibodies raised to Ob-R. Antibodies having light chains with 100% sequence identity are indicated in blackened boxes. Antibodies having light chains with 98-99% sequence identity are indicated in white boxes. The antibody clone identity is indicated below the matrix.

I. Definitions

Figure 1C:
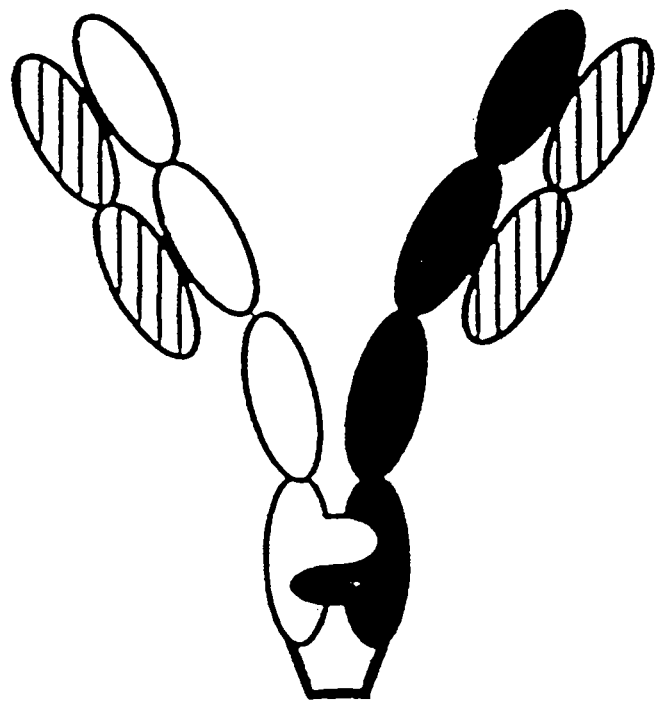

In general, the following words or phrases have the indicated definitions when used in the description, examples, and claims:

A "heteromultimer", "heteromultimeric polypeptide", or "heteromultimeric multispecific antibody" is a molecule comprising at least a first polypeptide and a second polypeptide, wherein the second polypeptide differs in amino acid sequence from the first polypeptide by at least one amino acid residue. Preferably, the heteromultimer has binding specificity for at least two different ligands or binding sites. The heteromultimer can comprise a "heterodimer" formed by the first and second polypeptide or can form higher order tertiary structures where polypeptides in addition to the first and second polypeptide are present. Exemplary structures for the heteromultimer include heterodimers (e.g. the bispecific immunoadhesin described by Dietsch et al., supra), heterotrimers (e.g. the Ab/Ia chimera described by Chamow et al., supra), heterotetramers (e.g. a bispecific antibody) and further oligomeric structures.

As used herein, "multimerization domain" refers to a region of each of the polypeptides of the heteromultimer. The "multimerization domain" promotes stable interaction of the chimeric molecules within the heteromultimer complex. Preferably, the multimerization domain promotes interaction between a specific first polypeptide and a specific second polypeptide, thereby enhancing the formation of the desired heteromultimer and substantially reducing the probability of the formation of undesired heteromultimers or homomultimers. The multimerization domains may interact via an immunoglobulin sequence, leucine zipper, a hydrophobic region, a hydrophilic region, or a free thiol which forms an intermolecular disulfide bond between the chimeric molecules of the chimeric heteromultimer. The free thiol may be introduced into the interface of one or more interacting polypeptides by substituting a naturally occurring residue of the polypeptide with, for example, a cysteine at a position allowing for the formation of a disulfide bond between the polypeptides. The multimerization domain may comprise an immunoglobulin constant region. A possible multimerization domain useful in the present invention is disclosed in PCT/US90/06849 (herein incorporated by reference in its entirety) in which hybrid immunoglobulins are described. In addition a multimerization region may be engineered such that steric interactions not only promote stable interaction, but further promote the formation of heterodimers over homodimers from a mixture of monomers. See, for example, PCT/US96/01598 (herein incorporated by reference in its entirety) in which a "protuberance-into-cavity" strategy is disclosed for an interface between a first and second polypeptide for hetero-oligomerization. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). The immunoglobulin sequence preferably, but not necessarily, is an immunoglobulin constant domain. The immunoglobulin moiety in the chimeras of the present invention may be obtained from $IgG_1$, $IgG_2$, $IgG_3$ or $IgG_4$ subtypes, IgA, IgE, IgD or IgM, but preferably $IgG_1$, $IgG_2$, $IgG_3$ or $IgG_4$.

By "free thiol-containing compound" is meant a compound that can be incorporated into or reacted with an amino acid of a polypeptide interface of the invention such that the free thiol moiety of the compound is positioned to interact with a free thiol of moiety at the interface of additional polypeptide of the invention to form a disulfide bond. Preferably, the free thiol-containing compound is cysteine.

The term "epitope tagged" when used herein refers to a chimeric polypeptide comprising the entire chimeric heteroadhesin, or a fragment thereof, fused to a "tag polypeptide". The tag polypeptide has enough residues to provide an epitope against which an antibody can be made, yet is short enough such that it does not interfere with activity of the chimeric heteroadhesin. The tag polypeptide preferably is fairly unique so that the antibody thereagainst does not substantially cross-react with other epitopes. Suitable tag polypeptides generally have at least 6 amino acid residues and usually between about 8-50 amino acid residues (preferably between about 9-30 residues). An embodiment of the invention encompasses a chimeric heteroadhesin linked to an epitope tag, which tag is used to detect the adhesin in a sample or recover the adhesin from a sample. As used herein, "common light chain" or "common amino acid sequence of the light chain" refers to the amino acid sequence of the light chain in the multispecific antibody of the invention. Panels of antibodies were generated against at least two different antigens by panning a phage display library such as that described by Vaughan, et al. (1996) supra, herein incorporated by reference in its entirety with particular reference to the method of selection of the phagemid library). The light chain sequences were compared with respect to the variable light chain amino acid sequences. Useful light chains from the compared panels are those having amino acid sequence identity of at least 80%, preferably at least 90%, more preferably at least 95%, and most preferably 100% identity. A common light chain sequence is a sequence designed to be an approximation of the two compared light chain sequences. Where the compared light chains are 100% sequence identical at the amino acid level, the common light chain is identical to the light chains from the selected library clones, even though the light chain functions in a different binding domain of the multispecific antibody. Where the compared light chains differ as described above, the common light chain may differ from one or the other, or both, of the compared light chains from the library clones. In a case in which the common light chain differs from one or the other, or both of the library clones, it is preferred that the differing residues occur outside of the antigen binding CDR residues of the antibody light chain. For example, the position of the antigen binding CDR residues may be determined according to a sequence definition (Kabat et al. (1991) supra) or structural definition (Chothia and Lesk (1987) J. Mol. Biol. 196:901-917).

As used herein, "amino acid sequence identity" refers to the percentage of the amino acids of one sequence are the same as the amino acids of a second amino acid sequence. 100% sequence identity between polypeptide chains means that the chains are identical.

As used herein, "polypeptide" refers generally to peptides and proteins having more than about ten amino acids. Preferably, mammalian polypeptides (polypeptides that were originally derived from a mammalian organism) are used, more preferably those which are directly secreted into the medium. Examples of bacterial polypeptides include, e.g., alkaline phosphatase and β-lactamase. Examples of mammalian polypeptides include molecules such as renin, a growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The "first polypeptide" is any polypeptide which is to be associated with a second polypeptide. The first and second polypeptide meet at an "interface" (defined below). In addition to the interface, the first polypeptide may comprise one or more additional domains, such as "binding domains" (e.g. an antibody variable domain, receptor binding domain, ligand binding domain or enzymatic domain) or antibody constant domains (or parts thereof) including $C_H2$, $C_H1$ and $C_L$ domains. Normally, the first polypeptide will comprise at least one domain which is derived from an antibody. This domain conveniently is a constant domain, such as the $C_H3$ domain of an antibody and can form the interface of the first polypeptide. Exemplary first polypeptides include antibody heavy chain polypeptides, chimeras combining an antibody constant domain with a binding domain of a heterologous polypeptide (i.e. an immunoadhesin, see definition below), receptor polypeptides (especially those which form dimers with another receptor polypeptide, e.g., interleukin-8 receptor (IL-8R) and integrin heterodimers (e.g. LFA-1 or GPIIIb/IIIa)), ligand polypeptides (e.g. nerve growth factor (NGF), neurotrophin-3 (NT-3), and brain-derived neurotrophic factor (BDNF)—see Arakawa et al. J. Biol. Chem. 269(45): 27833-27839 (1994) and Radziejewski et al. Biochem. 32(48): 1350 (1993)) and antibody variable domain polypeptides (e.g. diabodies). The preferred first polypeptide is selected from an antibody heavy chain fused to a constant domain of an immunoglobulin, wherein the constant domain has been altered at the interface to promote preferential interaction with a second polypeptide of the invention.

The "second polypeptide" is any polypeptide which is to be associated with the first polypeptide via an "interface". In addition to the interface, the second polypeptide may comprise additional domains such as a "binding domain" (e.g. an antibody variable domain, receptor binding domain, ligand binding domain or enzymatic domain), or antibody constant domains (or parts thereof) including $C_H2$, $C_H1$ and $C_L$ domains. Normally, the second polypeptide will comprise at least one domain which is derived from an antibody. This domain conveniently is a constant region, such as the $C_H3$ domain of an antibody and can form the interface of the second polypeptide. Exemplary second polypeptides include antibody heavy chain polypeptides, chimeras combining an antibody constant domain with a binding domain of a heterologous polypeptide (i.e. an immunoadhesin, see definition below), receptor polypeptides (especially those which form dimers with another receptor polypeptide, e.g., interleukin-8 receptor (IL-8R) and integrin heterodimers (e.g. LFA-1 or GPIIIb/IIIa)), ligand polypeptides (e.g. nerve growth factor (NGF), neurotrophin-3 (NT-3), and brain-derived neurotrophic factor (BDNF)— see Arakawa et al. J. Biol. Chem. 269(45):27833-27839 (1994) and Radziejewski et al. Biochem. 32(48):1350 (1993)) and antibody variable domain polypeptides (e.g. diabodies). The preferred second polypeptide is selected from an antibody heavy chain fused to a constant domain of an immunoglobulin, wherein the constant domain has been altered at the interface to promote preferential interaction with a first polypeptide of the invention.

A "binding domain" comprises any region of a polypeptide which is responsible for selectively binding to a molecule of interest (e.g. an antigen, ligand, receptor, substrate or inhibitor). Exemplary binding domains include an antibody variable domain, receptor binding domain, ligand binding domain and an enzymatic domain. In preferred embodiments, the binding domain includes an immunoglobulin heavy chain and light chain. According to the bispecific antibodies of the invention and the method of making them, the light chain for each binding domain of the bispecific antibody is a common light chain, thereby avoiding the formation of undesired hetermultimers in which mispairing of heavy and light chains occurs.

The term "antibody" as it refers to the invention shall mean a polypeptide containing one or more domains that bind an epitope on an antigen of interest, where such domain(s) are derived from or have sequence identity with the variable region of an antibody. Examples of antibodies include full length antibodies, antibody fragments, single chain molecules, bispecific or bifunctional molecules, diabodies, chimeric antibodies (e.g. humanized and PRIMATIZED™ antibodies), and immunoadhesins. "Antibody fragments" include Fv, Fv', Fab, Fab', and F(ab')$_2$ fragments.

"Humanized" forms of non-human (e.g. rodent or primate) antibodies are specific chimeric immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody preferably also will comprise at least a portion of an immunoglobulin constant region (Fc), typically that of a human immunoglobulin. The humanized antibody includes a PRIMATIZED™ antibody wherein the antigen-binding region of the antibody is derived from an antibody produced by immunizing macaque monkeys with the antigen of interest.

A "multispecific antibody" is a molecule having binding specificities for at least two different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, FcγRII or FcγRIII); BsAbs for use in therapy of infectious diseases such as anti-CD3/anti-herpes simplex virus (HSV), anti-T-cell receptor: CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants (see Fanger et al., supra); and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase (see Nolan et al., supra). Examples of trispecific antibodies include anti-CD3/anti-CD4/anti-CD37, anti-CD3/anti-CD5/anti-CD37 and anti-CD3/anti-CD8/anti-CD37.

As used herein, the term "immunoadhesin" designates antibody-like molecules which combine the "binding domain" of a heterologous protein (an "adhesin", e.g. a receptor, ligand or enzyme) with the effector functions of immunoglobulin constant domains. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as IgG$_1$, IgG$_2$, IgG$_3$, or IgG$_4$ subtypes, IgA, IgE, IgD or IgM.

The term "ligand binding domain" as used herein refers to any native cell-surface receptor or any region or derivative thereof retaining at least a qualitative ligand binding ability, and preferably the biological activity of a corresponding native receptor. In a specific embodiment, the receptor is from a cell-surface polypeptide having an extracellular domain which is homologous to a member of the immunoglobulin supergenefamily. Other typical receptors, are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "receptor binding domain" is used to designate any native ligand for a receptor, including cell adhesion molecules, or any region or derivative of such native ligand retaining at least a qualitative receptor binding ability, and preferably the biological activity of a corresponding native ligand. This definition, among others, specifically includes binding sequences from ligands for the above-mentioned receptors.

As used herein the phrase "multispecific immunoadhesin" designates immunoadhesins (as hereinabove defined) having at least two binding specificities (i.e. combining two or more adhesin binding domains). Multispecific immunoadhesins can be assembled as heterodimers, heterotrimers or heterotetramers, essentially as disclosed in WO 89/02922 (published 6 Apr. 1989), in EP 314,317 (published 3 May 1989), and in U.S. Pat. No. 5,116,964 issued 2 May 1992. Preferred multispecific immunoadhesins are bispecific. Examples of bispecific immunoadhesins include CD4-IgG/TNFreceptor-IgG and CD4-IgG/L-selectin-IgG. The last mentioned molecule combines the lymph node binding function of the lymphocyte homing receptor (LHR, L-selectin), and the HIV binding function of CD4, and finds potential application in the prevention or treatment of HIV infection, related conditions, or as a diagnostic.

An "antibody-immunoadhesin chimera (Ab/Ia chimera)" comprises a molecule which combines at least one binding domain of an antibody (as herein defined) with at least one immunoadhesin (as defined in this application). Exemplary Ab/Ia chimeras are the bispecific CD4-IgG chimeras described by Berg et al., supra and Chamow et al., supra.

The "interface" comprises those "contact" amino acid residues (or other non-amino acid groups such as carbohydrate groups, NADH, biotin, FAD or haem group) in the first polypeptide which interact with one or more "contact" amino acid residues (or other non-amino acid groups) in the interface of the second polypeptide. The preferred interface is a domain of an immunoglobulin such as a variable domain or constant domain (or regions thereof), however the interface between the polypeptides forming a heteromultimeric receptor or the interface between two or more ligands such as NGF, NT-3 and BDNF are included within the scope of this term. The preferred interface comprises the $C_H3$ domain of an immunoglobulin which preferably is derived from an IgG antibody and most preferably a human IgG$_1$ antibody.

An "original" amino acid residue is one which is replaced by an "import" residue which can have a smaller or larger side chain volume than the original residue. The import amino acid residue can be a naturally occurring or non-naturally occurring amino acid residue, but preferably is the former. "Naturally occurring" amino acid residues are those residues encoded by the genetic code and listed in Table 1 of PCT/US96/01598, herein incorporated by reference in its entirety. By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., Meth. Enzym. 202:301-336 (1991), for example. To generate such non-naturally occurring amino acid residues, the procedures of Noren et al. Science 244: 182 (1989) and Ellman et al., supra can be used. Briefly, this involves chemically activating a suppressor tRNA with a non-naturally occurring amino acid residue followed by in vitro transcription and translation of the RNA. The method of the instant invention involves replacing at least one original amino acid residue, but more than one original residue can be replaced. Normally, no more than the total residues in the interface of the first or second polypeptide will comprise original amino acid residues which are replaced. The preferred original residues for replacement are "buried". By "buried" is meant that the residue is essentially inaccessible to solvent. The preferred import residue is not cysteine to prevent possible oxidation or mispairing of disulfide bonds. By "original nucleic acid" is meant the nucleic acid encoding a polypeptide of interest which can be altered to encode within the multimerization domain amino acids whose side chains interact at the interface between the first and second polypeptide promoting stable interaction between the polypeptides. Such alterations may generate without limitation such stable interactions as protuberance-into-cavity, non-naturally occurring disulfide bonds, leucine zipper, hydrophobic interactions, and hydrophilic interations. Preferably, the alteration is chosen which promotes specific interaction between a first and second polypeptide of interest and effectively excludes interactions that result in undesired heteromer pairing or the formation of homomers. The original or starting nucleic acid may be a naturally occurring nucleic acid or may comprise a nucleic acid which has been subjected to prior alteration (e.g. a humanized antibody fragment). By "altering" the nucleic acid is meant that the original nucleic acid is genetically engineered or mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in Mutagenesis: a Practical Approach, M.J. McPherson, Ed., (IRL Press, Oxford, UK. (1991), and include site-directed mutagenesis, cassette mutagenesis and polymerase chain reaction (PCR) mutagenesis, for example.

The protuberance, cavity, or free thiol (such as a cysteine residue for disulfide bond formation) can be "introduced" into the interface of the first or second polypeptide by synthetic means, e.g. by recombinant techniques, in vitro peptide synthesis, those techniques for introducing non-naturally occurring amino acid residues previously described, by enzymatic or chemical coupling of peptides or some combination of these techniques. According, the protuberance, cavity or free thiol which is "introduced" is "non-naturally occurring" or "non-native", which means that it does not exist in nature or in the original polypeptide (e.g. a humanized monoclonal antibody). Preferably the import amino acid residue for forming the protuberance has a relatively small number of "rotamers" (e.g. about 3-6). A "rotamer" is an energetically favorable conformation of an amino acid side chain. The number of rotamers of the various amino acid residues are reviewed in Ponders and Richards, J. Mol. Biol. 193:775-791 (1987).

"Isolated" heteromultimer means heteromultimer which has been identified and separated and/or recovered from a component of its natural cell culture environment. Contaminant components of its natural environment are materials which would interfere with diagnostic or therapeutic uses for the heteromultimer, and may include enzymes, hormones, and other proteinaceous or nonproteinaceous solutes. In preferred embodiments, the heteromultimer will be purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. The heteromultimers of the present invention are generally purified to substantial homogeneity. The phrases "substantially homogeneous", "substantially homogeneous form" and "substantial homogeneity" are used to indicate that the product is substantially devoid of by-products originated from undesired polypeptide combinations (e.g. homomultimers). Expressed in terms of purity, substantial homogeneity means that the amount of by-products does not exceed 10%, and preferably is below 5%, more preferably below 1%, most preferably below 0.5%, wherein the percentages are by weight.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

II. Preparation of the Heteromultimer

1. Preparation of the Starting Materials

As a first step, the first and second polypeptide (and any additional polypeptides forming the heteromultimer) are selected. Normally, the nucleic acid encoding these polypeptides needs to be isolated so that it can be altered to encode the protuberance or cavity, or both, as herein defined. However, the mutations can be introduced using synthetic means, e.g. by using a peptide synthesizer. Also, in the case where the import residue is a non-naturally occurring residue, the method of Noren et al., supra is available for making polypeptides having such substitutions. Additionally, part of the heteromultimer is suitably made recombinantly in cell culture and other part(s) of the molecule are made by those techniques mentioned above. Techniques for isolating antibodies and preparing immunoadhesins follow. However, it will be appreciated that the heteromultimer can be formed from, or incorporate, other polypeptides using techniques which are known in the art. For example, nucleic acid encoding a polypeptide of interest (e.g. a ligand, receptor or enzyme) can be isolated from a cDNA library prepared from tissue believed to possess the polypeptide mRNA and to express it at a detectable level. Libraries are screened with probes (such as antibodies or oligonucleotides of about 20-80 bases) designed to identify the gene of interest or the protein encoded by it. Screening the cDNA or genomic library with the selected probe may be conducted using standard procedures as described in chapters 10-12 of Sambrook et al., Molecular Cloning: A Laboratory Manual (New York: Cold Spring Harbor Laboratory Press, 1989).

(I) Antibody Preparation

Several techniques for the production of antibodies have been described which include the traditional hybridoma method for making monoclonal antibodies, recombinant techniques for making antibodies (including chimeric antibodies, e.g. humanized antibodies), antibody production in transgenic animals and the recently described phage display technology for preparing "fully human" antibodies. These techniques shall be described briefly below. Polyclonal antibodies to the antigen of interest generally can be raised in animals by multiple subcutaneous (sC) or intraperitoneal (ip) injections of the antigen and an adjuvant. It may be useful to conjugate the antigen (or a fragment containing the target amino acid sequence) to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups. Animals are immunized against the immunogenic conjugates or derivatives by combining 1 mg of 1 µg of conjugate (for rabbits or mice, respectively) with 3 volumes of Freud's complete adjuvant and injecting the solution intradermally at multiple sites. One month later the animals are boosted with $\frac{1}{5}$ to $\frac{1}{10}$ the original amount of conjugate in Freud's complete adjuvant by subcutaneous injection at multiple sites. 7 to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are used to enhance the immune response.

Monoclonal antibodies are obtained from a population of substantially homogeneous antibodies using the hybridoma method first described by Kohler and Milstein, Nature 256: 495 (1975) or may be made by recombinant DNA methods (Cabilly et al., U.S. Pat. No. 4,816,567). In the hybridoma method, a mouse or other appropriate host animal, such as hamster, is immunized as hereinabove described to elicit lymphocytes that produce, or are capable of producing, antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63, Marcel Dekker, Inc., New York, 1987). See, also, Boerner et al., J. Immunol., 147(1):86-95 (1991) and WO 91/17769, published Nov. 28, 1991, for techniques for the production of human monoclonal antibodies. Culture medium in which hybridoma cells are growing is assayed for production of monoclonal antibodies directed against the antigen of interest. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson and Pollard, Anal. Biochem. 107:220 (1980). After hybridoma cells are identified that produce antibodies of the desired specificity, affinity, and/or activity, the clones may be subcloned by limiting dilution procedures and grown by standard methods. Goding, Monoclonal Antibodies: Principles and Practice, pp. 59-104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA 90:2551-255 (1993); Jakobovits et al., Nature 362:255-258 (1993); Fishwild, D. M., et al. (1996) Nat. Biotech 14:845-851; and Mendez, M. J., et al. (1997) Nat. Genetics 15:146-156).

In a further embodiment, antibodies or antibody fragments can be isolated from antibody phage libraries generated using the techniques described in McCafferty et al., Nature, 348: 552-554 (1990), using the antigen of interest to select for a suitable antibody or antibody fragment. Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Mark et al., Bio/Technol. 10:779-783 (1992)), as well as combinatorial infection and in vivo recombination as a strategy for constructing very large phage libraries (Waterhouse et al., Nuc. Acids Res., 21:2265-2266 (1993); Griffiths, A. D., et al. (1994) EMBO J. 13:3245-3260; and Vaughan, et al. (1996) supra). Thus, these techniques are viable alternatives to traditional monoclonal antibody hybridoma techniques for isolation of "monoclonal" antibodies (especially human antibodies) which are encompassed by the present invention.

DNA encoding the antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al., Proc. Nat. Acad. Sci. 81:6851 (1984). In that manner, "chimeric" antibodies are prepared that have the binding specificity of an anti-antigen monoclonal antibody herein.

Methods for humanizing non-human antibodies are well known in the art. Generally, a humanized antibody has one or more amino is acid residues introduced into it from a source which is non-human. Humanization can be performed essentially following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues, and possibly some FR residues, are substituted by residues from analogous sites in rodent antibodies. It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. For further details see WO 92/22653, published Dec. 23, 1992.

(ii) Immunoadhesin Preparation

Immunoglobulins (Ig) and certain variants thereof are known and many have been prepared in recombinant cell culture. For example, see U.S. Pat. No. 4,745,055; EP 256,654; Faulkner et al., Nature 298:286 (1982); EP 120,694; EP 125,023; Morrison, J. Immun. 123:793 (1979); Köhler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Natl. Acad. Sci. USA 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

Chimeras constructed from an adhesin binding domain sequence linked to an appropriate immunoglobulin constant domain sequence (immunoadhesins) are known in the art. Immunoadhesins reported in the literature include fusions of the T cell receptor (Gascoigne et al., Proc. Natl. Acad. Sci. USA 84:2936-2940 (1987)); CD4 (Capon et al., Nature 337:525-531 (1989); Traunecker et al., Nature 339:68-70 (1989); Zettmeissl et al., DNA Cell Biol. USA 9:347-353 (1990); and Byrn et al., Nature 344:667-670 (1990)); L-selectin (homing receptor) (Watson et al., J. Cell. Biol. 110:2221-2229 (1990); and Watson et al., Nature 349:164-167 (1991)); CD44 (Aruffo et al., Cell 61:1303-1313 (1990)); CD28 and B7 (Linsley et al., J. Exp. Med. 173:721-730 (1991)); CTLA-4 (Lisley et al., J. Exp. Med. 174:561-569 (1991)); CD22 (Stamenkovic et al., Cell 66:1133-1144 (1991)); TNF receptor (Ashkenazi et al., Proc. Natl. Acad. Sci. USA 88:10535-10539 (1991); Lesslauer et al., Eur. J. Immunol. 27:2883-2886 (1991); and Peppel et al., J. Exp. Med. 174:1483-1489 (1991)); and IgE receptor a (Ridgway and Gorman, J. Cell. Biol. Vol. 115, Abstract No. 1448 (1991)).

The simplest and most straightforward immunoadhesin design combines the binding domain(s) of the adhesin (e.g. the extracellular domain (ECD) of a receptor) with the hinge and Fc regions of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the Ia.

In a preferred embodiment, the adhesin sequence is fused to the N-terminus of the Fc domain of immunoglobulin $G_1$ ($IgG_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an $IgG_1$, $IgG_2$, or $IgG_3$ heavy chain. The precise site at which the fusion is made is not critical, and the optimal site can be determined by routine experimentation.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

(a) $AC_L$-$AC_L$;
(b) $AC_H$-[$AC_H$, $AC_L$-$AC_H$, $AC_L$-$V_HC_H$, or $V_LC_L$-$AC_H$];
(c) $AC_L$-$AC_H$-[$AC_L$-$AC_H$, $AC_L$-$V_HC_H$, $V_LC_L$-$AC_H$, or $V_LC_L$-$V_HC_H$];
(d) $AC_L$-$V_HC_H$-[$AC_H$, or $AC_L$-$V_HC_H$, or $V_LC_L$-$AC_H$];
(e) $V_LC_L$-$AC_H$-[$AC_L$-$V_HC_H$ (or $V_LC_L$-$AC_H$]; and
(f) $[A-Y]_n$-$[V_LC_L$-$V_HC_H]_2$, wherein each A represents identical or different adhesin amino acid sequences;
$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et al., Mol. Immunol. 28:1027-1037 (1991).

An immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

In a preferred embodiment, the immunoglobulin sequences used in the construction of the immunoadhesins of the present invention are from an IgG immunoglobulin heavy chain constant domain. For human immunoadhesins, the use of human $IgG_1$ and $IgG_3$ immunoglobulin sequences is preferred. A major advantage of using $IgG_1$ is that $IgG_1$ immunoadhesins can be purified efficiently on immobilized protein A. In contrast, purification of $IgG_3$ requires protein G, a significantly less versatile medium. However, other structural and functional properties of immunoglobulins should be considered when choosing the Ig fusion partner for a particular immunoadhesin construction. For example, the $IgG_3$ hinge is longer and more flexible, so it can accommodate larger "adhesin" domains that may not fold or function properly when fused to $IgG_1$. Another consideration may be valency; IgG immunoadhesins are bivalent homodimers, whereas Ig subtypes like IgA and IgM may give rise to dimeric or pentameric structures, respectively, of the basic Ig homodimer unit. For immunoadhesins designed for in vivo application, the pharmacokinetic properties and the effector functions specified by the Fc region are important as well. Although $IgG_1$, $IgG_2$ and $IgG_4$ all have in vivo half-lives of 21 days, their relative potencies at activating the complement system are different. $IgG_4$ does not activate complement, and $IgG_2$ is significantly weaker at complement activation than $IgG_1$. Moreover, unlike $IgG_1$, $IgG_2$ does not bind to Fc receptors on mononuclear cells or neutrophils. While $IgG_3$ is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, $IgG_1$ has only four serologically-defined allotypic sites, two of which (G1m and 2) are located in the Fc region; and one of these sites, G1m1, is non-immunogenic. In contrast, there are 12 serologically-defined allotypes in IgG3, all of which are in the Fc region; only three of these sites (G3 m5, 11 and 21) have one allotype which is nonimmunogenic. Thus, the potential immunogenicity of a γ3 immunoadhesin is greater than that of a γ1 immunoadhesin.

Immunoadhesins are most conveniently constructed by fusing the cDNA sequence encoding the adhesin portion in-frame to an Ig cDNA sequence. However, fusion to genomic Ig fragments can also be used (see, e.g. Gascoigne et al., supra; Aruffo et al., Cell 61:1303-1313 (1990); and Stamenkovic et al., Cell 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the Ig parts of the immunoadhesin are inserted in tandem into a plasmid vector that directs efficient expression in the chosen host cells.

2. Generating a Protuberance and/or Cavity

As a first step to selecting original residues for forming the protuberance and/or cavity, the three-dimensional structure of the heteromultimer is obtained using techniques which are well known in the art such as X-ray crystallography or NMR. Based on the three-dimensional structure, those skilled in the art will be able to identify the interface residues. The preferred interface is the $C_H3$ domain of an immunoglobulin constant domain. The interface residues of the $C_H3$ domains of IgG, IgA, IgD, IgE and IgM have been identified (see, for example, PCT/US96/01598, herein incorporated by reference in its entirety), including those which are optimal for replacing with import residues; as were the interface residues of various IgG subtypes and "buried" residues. The basis for engineering the $C_H3$ interface is that X-ray crystallography has demonstrated that the intermolecular association between human $IgG_1$ heavy chains in the Fc region includes extensive protein/protein interaction between $C_H3$ domains whereas the glycosylated $C_H2$ domains interact via their carbohydrate (Deisenhofer, Biochem. 20:2361-2370 (1981)). In addition there are two inter-heavy chain disulfide bonds which are efficiently formed during antibody expression in mammalian cells unless the heavy chain is truncated to remove $C_H2$ and $C_H3$ domains (King et al., Biochem. J. 281:317 (1992)). Thus, heavy chain assembly appears to promote disulfide bond formation rather than vice versa. Taken together these structural and functional data led to the hypothesis that antibody heavy chain association is directed by the $C_H3$ domains. It was further speculated that the interface between $C_H3$ domains might be engineered to promote formation of heteromultimers of different heavy chains and hinder assembly of corresponding homomultimers. The experiments described herein demonstrated that it was possible to promote the formation of heteromultimers over homomultimers using this approach. Thus, it is possible to generate a polypeptide fusion comprising a polypeptide of interest and the $C_H3$ domain of an antibody to form a first or second polypeptide. The preferred $C_H3$ domain is derived from an IgG antibody, such as an human $IgG_1$. Those interface residues which can potentially constitute candidates for forming the protuberance or cavity are identified. It is preferable to select "buried" residues to be replaced. To determine whether a residue is buried, the surface accessibility program of Lee et al. J. Mol. Biol. 55:379-400 (1971) can be used to calculate the solvent accessibility (SA) of residues in the interface. Then, the SA for the residues of each of the first and second polypeptide can be separately calculated after removal of the other polypeptide. The difference in SA of each residue between the monomer and dimer forms of the interface can then be calculated using the equation: SA (dimer)-SA (monomer). This provides a list of residues which lose SA on formation of the dimer. The SA of each residue in the dimer is compared to the theoretical SA of the same amino acid in the tripeptide Gly-X-Gly, where X=the amino acid of interest (Rose et al. Science 229:834-838 (1985)). Residues which (a) lost SA in the dimer compared to the monomer and (b) had an SA less than 26% of that in their corresponding tripeptide are considered as interface residues. Two categories may be delineated: those which have an SA<10% compared to their corresponding tripeptide (i.e. "buried") and those which have 25%>SA>10% compared to their corresponding tripeptide (i.e. "partially buried") (see Table 1, below).

TABLE 1

| Residue No.[†] | SA Lost Monomer → Dimer | | % Tripeptide | |
| --- | --- | --- | --- | --- |
| | Polypeptide A | Polypeptide B | Polypeptide A | Polypeptide B |
| Q347 | 22.1 | 31.0 | 25.0 | 26.5 |
| Y349 | 79.8 | 83.9 | 5.2 | 5.7 |
| L351 | 67.4 | 77.7 | 3.9 | 2.0 |
| S354 | 53.4 | 52.8 | 11.3 | 11.7 |
| E357 | 43.7 | 45.3 | 0.4 | 1.3 |
| S364 | 21.5 | 15.1 | 0.5 | 1.4 |
| T366 | 29.3 | 25.8 | 0.0 | 0.1 |
| L368 | 25.5 | 29.7 | 1.0 | 1.1 |
| K370 | 55.8 | 62.3 | 11.5 | 11.0 |
| T394 | 64.0 | 58.5 | 0.6 | 1.4 |
| V397 | 50.3 | 49.5 | 13.2 | 11.0 |
| D399 | 39.7 | 33.7 | 5.7 | 5.7 |
| F405 | 53.7 | 52.1 | 0.0 | 0.0 |
| Y407 | 89.1 | 90.3 | 0.0 | 0.0 |
| K409 | 86.8 | 92.3 | 0.7 | 0.6 |
| T411 | 4.3 | 7.5 | 12.7 | 9.8 |

[†]residue numbering as in IgG crystal structure (Deisenhofer, Biochemistry 20: 2361-2370 (1981)).

The effect of replacing residues on the polypeptide chain structure can be studied using a molecular graphics modeling program such as the Insight™ program (Biosym Technologies). Using the program, those buried residues in the interface of the first polypeptide which have a small side chain volume can be changed to residues having a larger side chain volume (i.e. a protuberance), for example. Then, the residues in the interface of the second polypeptide which are in proximity to the protuberance are examined to find a suitable residue for forming the cavity. Normally, this residue will have a large side chain volume and is replaced with a residue having a smaller side chain volume. In certain embodiments, examination of the three-dimensional structure of the interface will reveal a suitably positioned and dimensioned protuberance on the interface of the first polypeptide or a cavity on the interface of the second polypeptide. In these instances, it is only necessary to model a single mutant, i.e., with a synthetically introduced protuberance or cavity.

With respect to selecting potential original residues for replacement where the first and second polypeptide each comprise a $C_H3$ domain, the $C_H3/C_H3$ interface of human IgG$_1$ involves sixteen residues on each domain located on four anti-parallel β-strands which buries 1090 Å$^2$ from each surface (Deisenhofer, supra) and Miller, J. Mol. Biol. 216:965 (1990)). Mutations are preferably targeted to residues located on the two central anti-parallel β-strands. The aim is to minimize the risk that the protuberances which are created can be accommodated by protruding into surrounding solvent rather than by compensatory cavities in the partner $C_H3$ domain.

Once the preferred original/import residues are identified by molecular modeling, the amino acid replacements are introduced into the polypeptide using techniques which are well known in the art. Normally the DNA encoding the polypeptide is genetically engineered using the techniques described in *Mutagenesis: a Practical Approach*, supra.

Oligonucleotide-mediated mutagenesis is a preferred method for preparing substitution variants of the DNA encoding the first or second polypeptide. This technique is well known in the art as described by Adelman et al., DNA, 2:183 (1983). Briefly, first or second polypeptide DNA is altered by hybridizing an oligonucleotide encoding the desired mutation to a DNA template, where the template is the single-stranded form of a plasmid or bacteriophage containing the unaltered or native DNA sequence of heteromultimer. After hybridization, a DNA polymerase is used to synthesize an entire second complementary strand of the template that will thus incorporate the oligonucleotide primer, and will code for the selected alteration in the heteromultimer DNA.

Cassette mutagenesis can be performed as described Wells et al. Gene 34:315 (1985) by replacing a region of the DNA of interest with a synthetic mutant fragment generated by annealing complimentary oligonucleotides. PCR mutagenesis is also suitable for making variants of the first or second polypeptide DNA. While the following discussion refers to DNA, it is understood that the technique also finds application with RNA. The PCR technique generally refers to the following procedure (see Erlich, Science, 252:1643-1650 (1991), the chapter by R. Higuchi, p. 61-70).

This invention also encompasses, in addition to the protuberance or cavity mutations, amino acid sequence variants of the heteromultimer which can be prepared by introducing appropriate nucleotide changes into the heteromultimer DNA, or by synthesis of the desired heteromultimer polypeptide. Such variants include, for example, deletions from, or insertions or substitutions of, residues within the amino acid sequences of the first and second polypeptides forming the heteromultimer. Any combination of deletion, insertion, and substitution is made to arrive at the final construct, provided that the final construct possesses the desired antigen-binding characteristics. The amino acid changes also may alter post-translational processes of the heteromultimer, such as changing the number or position of glycosylation sites.

A useful method for identification of certain residues or regions of the heteromultimer polypeptides that are preferred locations for mutagenesis is called "alanine scanning mutagenesis," as described by Cunningham and Wells, Science, 244:1081-1085 (1989). Here, a residue or group of target residues are identified (e.g. charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined.

Normally the mutations will involve conservative amino acid replacements in non-functional regions of the heteromultimer. Exemplary mutations are shown in Table 2.

TABLE 2

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Covalent modifications of the heteromultimer polypeptides are included within the scope of this invention. Covalent modifications of the heteromultimer can be introduced into the molecule by reacting targeted amino acid residues of the heteromultimer or fragments thereof with an organic derivatizing agent that is capable of reacting with selected side chains or the N- or C-terminal residues. Another type of covalent modification of the heteromultimer polypeptide included within the scope of this invention comprises altering the native glycosylation pattern of the polypeptide. By altering is meant deleting one or more carbohydrate moieties found in the original heteromultimer, and/or adding one or more glycosylation sites that are not present in the original heteromultimer. Addition of glycosylation sites to the heteromultimer polypeptide is conveniently accomplished by altering the amino acid sequence such that it contains one or more N-linked glycosylation sites. The alteration may also be made by the addition of, or substitution by, one or more serine or threonine residues to the original heteromultimer sequence (for O-linked glycosylation sites). For ease, the heteromultimer amino acid sequence is preferably altered through changes at the DNA level, particularly by mutating the DNA encoding the heteromultimer polypeptide at preselected bases such that codons are generated that will translate into the desired amino acids. Another means of increasing the number of carbohydrate moieties on the heteromultimer polypeptide is by chemical or enzymatic coupling of glycosides to the polypeptide. These methods are described in WO 87/05330 published 11 Sep. 1987, and in Aplin and Wriston, CRC Crit. Rev. Biochem., pp. 259-306 (1981). Removal of carbohydrate moieties present on the heteromultimer may be accomplished chemically or enzymatically.

Another type of covalent modification of heteromultimer comprises linking the heteromultimer polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Since it is often difficult to predict in advance the characteristics of a variant heteromultimer, it will be appreciated that some screening of the recovered variant will be needed to select the optimal variant.

3. Expression of Heteromultimer Having Common Light Chains

Following mutation of the DNA and selection of the common light chain as disclosed herein, the DNA encoding the molecules is expressed using recombinant techniques which are widely available in the art. Often, the expression system of choice will involve a mammalian cell expression vector and host so that the heteromultimer is appropriately glycosylated (e.g. in the case of heteromultimers comprising antibody domains which are glycosylated). However, the molecules can also be produced in the prokaryotic expression systems elaborated below. Normally, the host cell will be transformed with DNA encoding both the first polypeptide, the second polypeptide, the common light chain polypeptide, and other polypeptide(s) required to form the heteromultimer, on a single vector or independent vectors. However, it is possible to express the first polypeptide, second polypeptide, and common light chain polypeptide (the heteromultimer components) in independent expression systems and couple the expressed polypeptides in vitro.

The nucleic acid(s) (e.g., cDNA or genomic DNA) encoding the heteromultimer and common light chain is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

The polypeptides of the heteromultimer components may be produced as fusion polypeptides with a signal sequence or other polypeptide having a specific cleavage site at the N-terminus of the mature protein or polypeptide. In general, the signal sequence may be a component of the vector, or it may be a part of the DNA that is inserted into the vector. The heterologous signal sequence selected preferably is one that is recognized and processed (i.e., cleaved by a signal peptidase) by the host cell. For prokaryotic host cells, the signal sequence may be substituted by a prokaryotic signal sequence selected, for example, from the group of the is alkaline phosphatase, penicillinase, lpp, or heat-stable enterotoxin II leaders. For yeast secretion the native signal sequence may be substituted by, e.g., the yeast invertase leader, alpha factor leader (including *Saccharomyces* and *Kluyveromyces* α-factor leaders, the latter described in U.S. Pat. No. 5,010,182 issued 23 Apr. 1991), or acid phosphatase leader, the *C. albicans* glucoamylase leader (EP 362,179 published 4 Apr. 1990), or the signal described in WO 90/13646 published 15 Nov. 1990. In mammalian cell expression the native signal sequence (e.g., the antibody or adhesin presequence that normally directs secretion of these molecules from human cells in vivo) is satisfactory, although other mammalian signal sequences may be suitable as well as viral secretory leaders, for example, the herpes simplex gD signal. The DNA for such precursor region is ligated in reading frame to DNA encoding the polypeptides forming the heteromultimer.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors should contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin (Southern et al., J. Molec. Appl. Genet. 1:327 (1982)), mycophenolic acid (Mulligan et al., Science 209:1422 (1980)) or hygromycin (Sugden et al., Mol. Cell. Biol. 5:410-413 (1985)). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the heteromultimer nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes heteromultimer. Increased quantities of heteromultimer are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, Proc. Natl. Acad. Sci. USA 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the components of the heteromultimer. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding heteromultimer, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature 282:39 (1979); Kingsman et al., Gene 7:141 (1979); or Tschemper et al., Gene 10:157 (1980)). The trp1 gene provides a selection marker for a mutant strain of yeast lacking the ability to grow in tryptophan, for example, ATCC No. 44076 or PEP4-1 (Jones, Genetics 85:12 (1977)). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts. Bianchi et al., Curr. Genet. 12:185 (1987). More recently, an expression system for large-scale production of recombinant calf chymosin was reported for K. lactis. Van den Berg, Bio/Technology 8:135 (1990). Stable multi-copy expression vectors for secretion of mature recombinant human serum albumin by industrial strains of Kluyveromyces have also been disclosed (Fleer et al., Bio/Technology 9:968-975 (1991)).

Expression and cloning vectors usually contain a promoter that is recognized by the host organism and is operably linked to the heteromultimer nucleic acid. A large number of promoters recognized by a variety of potential host cells are well known. These promoters are operably linked to heteromultimer-encoding DNA by removing the promoter from the source DNA by restriction enzyme digestion and inserting the isolated promoter sequence into the vector.

Promoters suitable for use with prokaryotic hosts include the β-lactamase and lactose promoter systems (Chang et al., Nature 275:615 (1978); and Goeddel et al., Nature 281:544 (1979)), alkaline phosphatase, a tryptophan (trp) promoter system (Goeddel, Nucleic Acids Res., 8:4057 (1980) and EP 36,776) and hybrid promoters such as the tac promoter (deBoer et al., Proc. Natl. Acad. Sci. USA 80:21-25 (1983)). However, other known bacterial promoters are suitable. Their nucleotide sequences have been published, thereby enabling a skilled worker operably to ligate them to DNA encoding the heteromultimer (Siebenlist et al., Cell 20:269 (1980)) using linkers or adaptors to supply any required restriction sites. Promoters for use in bacterial systems also will contain a Shine-Dalgarno (S.D.) sequence operably linked to the DNA encoding the heteromultimer.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., J. Biol. Chem. 255:2073 (1980)) or other glycolytic enzymes (Hess et al., J. Adv. Enzyme Reg. 7:149 (1968); and Holland, Biochemistry 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Heteromultimer transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter or from heat-shock promoters.

The early and late promoters of the SV40 virus are conveniently obtained as an SV40 restriction fragment that also contains the SV40 viral origin of replication. Fiers et al., Nature 273:113 (1978); Mulligan and Berg, Science 209: 1422-1427 (1980); Pavlakis et al., Proc. Natl. Acad. Sci. USA 78:7398-7402 (1981). The immediate early promoter of the human cytomegalovirus is conveniently obtained as a HindIII E restriction fragment. Greenaway et al., Gene 18:355-360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., Nature 295:503-508 (1982) on expressing cDNA encoding immune interferon in monkey cells; Reyes et al., Nature 297: 598-601 (1982) on expression of human β-interferon cDNA in mouse cells under the control of a thymidine kinase promoter from herpes simplex virus; Canaani and Berg, Proc. Natl. Acad. Sci. USA 79:5166-5170 (1982) on expression of the human interferon β1 gene in cultured mouse and rabbit cells; and Gorman et al., Proc. Natl. Acad. Sci. USA 79:6777-6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of DNA encoding the heteromultimer components by higher eukaryotes is often increased by inserting an enhancer sequence into the vector. Enhancers are relatively orientation and position independent, having been found 5' (Laimins et al., Proc. Natl. Acad. Sci. USA 78:993 (1981)) and 3' (Lusky et al., Mol. Cell. Bio. 3:1108 (1983)) to the transcription unit, within an intron (Banerji et al., Cell 33:729

(1983)), as well as within the coding sequence itself (Osborne et al., Mol. Cell. Bio. 4:1293 (1984)). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the heteromultimer-encoding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the heteromultimer.

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., Nucleic Acids Res. 9:309 (1981) or by the method of Maxam et al., Methods in Enzymology 65:499 (1980).

Particularly useful in the practice of this invention are expression vectors that provide for the transient expression in mammalian cells of DNA encoding heteromultimer. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17-16.22. Transient expression systems, comprising a suitable expression vector and a host cell, allow for the convenient positive identification of polypeptides encoded by cloned DNAs, as well as for the rapid screening of heteromultimers having desired binding specificities/affinities or the desired gel migration characteristics relative to heteromultimers or homomultimers lacking the non-natural disulfide bonds generated according to the instant invention.

Other methods, vectors, and host cells suitable for adaptation to the synthesis of the heteromultimer in recombinant vertebrate cell culture are described in Gething et al., Nature 293:620-625 (1981); Mantei et al., Nature 281:40-46 (1979); EP 117,060; and EP 117,058. A particularly useful plasmid for mammalian cell culture expression of the heteromultimer is pRK5 (EP 307,247) or pSVI6B (PCT pub. no. WO 91/08291 published 13 Jun. 1991).

The choice of host cell line for the expression of heteromultimer depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient heteromultimer expression. CDM8-based vectors can be used to transfect COS cells by the DEAE-dextran method (Aruffo et al., Cell 61:1303-1313 (1990); and Zettmeissl et al., DNA Cell Biol. (US) 9:347-353 (1990)). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture. These clones are grown in the presence of increasing levels of DHFR inhibitor methotrexate and clones are selected in which the number of gene copies encoding the DHFR and heteromultimer sequences is co-amplified. If the immunoadhesin contains a hydrophobic leader sequence at its N-terminus, it is likely to be processed and secreted by the transfected cells. The expression of immunoadhesins with more complex structures may require uniquely suited host cells. For example, components such as light chain or J chain may be provided by certain myeloma or hybridoma host cells (Gascoigne et al., supra; and Martin et al., J. Virol. 67:3561-3568 (1.993)).

Other suitable host cells for cloning or expressing the vectors herein are prokaryote, yeast, or other higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains.such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonAΔ ptr3 phoAΔE15 Δ(argF-lac)169 ompTΔ degP41kan'. Strain 27C7 was deposited on 30 Oct. 1991 in the American Type Culture Collection as ATCC No. 55,244. Alternatively, the strain of *E. coli* having mutant periplasmic protease disclosed in U.S. Pat. No. 4,946,783 issued 7 Aug. 1990 may be employed. Alternatively, methods of cloning, e.g., PCR or other nucleic acid polymerase reactions, are suitable.

In addition to prokaryotes, eukaryotic microbes such as filamentous fungi or yeast are suitable cloning or expression hosts for heteromultimer-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, Nature 290:140 (1981); EP 139,383 published May 2, 1985); *Kluyveromyces* hosts (U.S. Pat. No. 4,943,529; Fleer et al., supra) such as, e.g., *K. lactis* (MW98-8C, CBS683, CBS4574; Louvencourt et al., J. Bacteriol., 737 (1983)), *K. fragilis* (ATCC 12,424), *K. bulgaricus*

(ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus; yarrowia* (EP 402,226); *Pichia pastoris* (EP 183,070; Sreekrishna et al., J. Basic Microbiol. 28:265-278 (1988)); *Candida; Trichoderma reesia* (EP 244,234); *Neurospora crassa* (Case et al., Proc. Natl. Acad. Sci. USA 76:5259-5263 (1979)); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., Biochem. Biophys. Res. Commun. 112:284-289 (1983); Tilburn et al., Gene 26:205-221 (1983); Yelton et al., Proc. Natl. Acad. Sci. USA 81:1470-1474 (1984)) and *A. niger* (Kelly and Hynes, EMBO J. 4:475-479 (1985)).

Suitable host cells for the expression of glycosylated heteromultimer are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., Bio/Technology 6:47-55 (1988); Miller et al., in Genetic Engineering, Setlow et al., eds., Vol. 8 (Plenum Publishing, 1986), pp. 277-279; and Maeda et al., Nature 315:592-594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the heteromultimer DNA. During incubation of the plant cell culture with *A. tumefaciens*, the DNA encoding the heteromultimer is transferred to the plant cell host such that it is transfected, and will, under appropriate conditions, express the heteromultimer DNA. In addition, regulatory and signal sequences compatible with plant cells are available, such as the nopaline synthase promoter and polyadenylation signal sequences. Depicker et al., J. Mol. Appl. Gen. 1:561 (1982). In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

The preferred hosts are vertebrate cells, and propagation of vertebrate cells in culture (tissue culture) has become a routine procedure in recent years (Tissue Culture, Academic Press, Kruse and Patterson, editors (1973)). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR(CHO, Urlaub and Chasin, Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transfected with the above-described expression or cloning vectors of this invention and cultured in conventional nutrient media modified as appropriate for inducing promoters, selecting transformants, or amplifying the genes encoding the desired sequences. Depending on the host cell used, transfection is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., Gene 23:315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, Virology 52:456-457 (1978) is preferred. General aspects of mammalian cell host system transformations have been described by Axel in U.S. Pat. No. 4,399,216 issued 16 Aug. 1983. Transformations into yeast are typically carried out according to the method of Van Solingen et al., J. Bact. 130: 946 (1977) and Hsiao et al., Proc. Natl. Acad. Sci. (USA) 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., Methods in Enzymology (1989), Keown et al., Methods in Enzymology 185:527-537 (1990), and Mansour et al., Nature 336:348-352 (1988).

Prokaryotic cells used to produce the heteromultimer polypeptide of this invention are cultured in suitable media as described generally in Sambrook et al., supra.

The mammalian host cells used to produce the heteromultimer of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace, Meth. Enz. 58:44 (1979), Barnes and Sato, Anal. Biochem. 102:255 (1980), U.S. Pat. Nos. 4,767,704; 4,657,866; 4,927, 762; or 4,560,655; WO 90/03430; WO 87/00195; U.S. Pat. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in Mammalian Cell Biotechnology: a Practical Approach, M. Butler, ed., IRL Press, 1991.

The host cells referred to in this disclosure encompass cells in culture as well as cells that are within a host animal.

4. Recovery of the Heteromultimer

The heteromultimer preferably is generally recovered from the culture medium as a secreted polypeptide, although it also may be recovered from host cell lysate when directly produced without a secretory signal. If the heteromultimer is membrane-bound, it can be released from the membrane using a suitable detergent solution (e.g. Triton-X 100).

When the heteromultimer is produced in a recombinant cell other than one of human origin, it is completely free of proteins or polypeptides of human origin. However, it is necessary to purify the heteromultimer from recombinant cell proteins or polypeptides to obtain preparations that are substantially homogeneous as to heteromultimer. As a first step, the culture medium or lysate is normally centrifuged to remove particulate cell debris.

Heterodimers having antibody constant domains can be conveniently purified by hydroxylapatite chromatography, gel electrophoresis, dialysis, or affinity chromatography, with affinity chromatography being the preferred purification technique. Where the heteromultimer comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin Sepharose, chromatography on an anion or cation exchange resin (such as a polyaspartic acid column), chromatofocusing, SDS-PAGE, and ammonium sulfate precipitation are also available depending on the polypeptide to be recovered. The suitability of protein A as an affinity ligand depends on the species and isotype of the immunoglobulin Fc domain that is used in the chimera. Protein A can be used to purify immunoadhesins that are based on human $\gamma1$, $\gamma2$, or $\gamma4$ heavy chains (Lindmark et al., J. Immunol. Meth. 62:1-13 (1983)). Protein G is recommended for all mouse isotypes and for human $\gamma3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human $\gamma1$ molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in a heterodimer preparation that is >95% pure.

5. Uses for a Heteromultimeric Multispecific Antibody Having Common Light Chains Many therapeutic applications for the heteromultimer are contemplated. For example, the heteromultimer can be used for redirected cytotoxicity (e.g. to kill tumor cells), as a vaccine adjuvant, for delivering thrombolytic agents to clots, for converting enzyme activated prodrugs at a target site (e.g. a tumor), for treating infectious diseases, targeting immune complexes to cell surface receptors, or for delivering immunotoxins to tumor cells. For example, tumor vasculature targeting has been accomplished by targeting a model endothelial antigen, class II major histocompatibility complex, with an antibody-ricin immunotoxin (Burrows, F.J. and Thorpe, P.E. (1993) Proc Natl Acad Sci USA 90:8996-9000). Significantly greater efficacy was achieved by combining the anti-endothelial immunotoxin with a second immunotoxin directed against the tumor cells themselves (Burrows, F. J. and Thorpe, P. E. (1993) supra). Recently, tissue factor was successfully targeted to tumor vasculature using a bispecific antibody, triggering local thrombosis that resulted in significant anti-tumor efficacy (Huang, X. et al. (1997) Science 275:547-550). In addition, bispecific diabodies have been used successfully to direct cytotoxic T-cells to kill target breast tumor cells and B-cell lymphoma cells in vitro (Zhu, Z. et al. (1996) Bio/Technology 14:192-196; and Holliger, P. et al. (1996) Protein Engin. 9:299-305).

Therapeutic formulations of the heteromultimer are prepared for storage by mixing the heteromultimer having the desired degree of purity with optional physiologically acceptable carriers, excipients, or stabilizers (Remington's Pharmaceutical Sciences, 16th edition, Osol, A., Ed., (1980)), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The heteromultimer also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, supra.

The heteromultimer to be used for in vivo administration must be sterile. This is readily accomplished by filtration through sterile filtration membranes, prior to or following lyophilization and reconstitution. The heteromultimer ordinarily will be stored in lyophilized form or in solution.

Therapeutic heteromultimer compositions generally are placed into a container having a sterile access port, for example, an intravenous solution bag or vial having a stopper pierceable by a hypodermic injection needle.

The route of heteromultimer administration is in accord with known methods, e.g., injection or infusion by intravenous, intraperitoneal, intracerebral, intramuscular, intraocular, intraarterial, or intralesional routes, or by sustained release systems as noted below. The heteromultimer is administered continuously by infusion or by bolus injection.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., J. Biomed. Mater. Res. 15:167-277 (1981) and Langer, Chem. Tech. 12:98-105 (1982) or poly(vinylalcohol)), polylactides (U.S. Pat. No. 3,773,919, EP 58,481), copolymers of L-glutamic acid and gamma ethyl-L-glutamate (Sidman et al., Biopolymers 22:547-556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release heteromultimer compositions also include liposomally entrapped heteromultimer. Liposomes containing heteromultimer are prepared by methods known per se: DE 3,218,121; Epstein et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the optimal heteromultimer therapy.

An effective amount of heteromultimer to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 10 mg/kg or more, depending on the factors mentioned above. Typically, the clinician will administer heteromultimer until a dosage is reached that achieves the desired effect. The progress of this therapy is easily monitored by conventional assays.

The heteromultimers described herein can also be used in enzyme immunoassays. To achieve this, one arm of the heteromultimer can be designed to bind to a specific epitope on the enzyme so that binding does not cause enzyme inhibition, the other arm of the heteromultimer can be designed to bind to the immobilizing matrix ensuring a high enzyme density at the desired site. Examples of such diagnostic heteromultimers include those having specificity for IgG as well as ferritin, and those having binding specificities for horse radish peroxidase (HRP) as well as a hormone, for example.

The heteromultimers can be designed for use in two-site immunoassays. For example, two bispecific heteromultimers are produced binding to two separate epitopes on the analyte protein—one heteromultimer binds the complex to an insoluble matrix, the other binds an indicator enzyme.

Heteromultimers can also be used for in vitro or in vivo immunodiagnosis of various diseases such as cancer. To facilitate this diagnostic use, one arm of the heteromultimer can be designed to bind a tumor associated antigen and the other arm can bind a detectable marker (e.g. a chelator which binds a radionuclide). For example, a heteromultimer having specificities for the tumor associated antigen CEA as well as a bivalent hapten can be used for imaging of colorectal and thyroid carcinomas. Other non-therapeutic, diagnostic uses for the heteromultimer will be apparent to the skilled practitioner.

For diagnostic applications, at least one arm of the heteromultimer typically will be labeled directly or indirectly with a detectable moiety. The detectable moiety can be any one which is capable of producing, either directly or indirectly, a detectable signal. For example, the detectable moiety may be a radioisotope, such as $^{3}H$, $^{14}C$, $^{32}P$, $^{35}S$, or $^{125}I$; a fluorescent or chemiluminescent compound, such as fluorescein isothiocyanate, rhodamine, or luciferin; or an enzyme, such as alkaline phosphatase, beta-galactosidase or horseradish peroxidase (HRP).

Any method known in the art for separately conjugating the heteromultimer to the detectable moiety may be employed, including those methods described by Hunter et al., Nature 144:945 (1962); David et al., Biochemistry 13:1014 (1974); Pain et al., J. Immunol. Meth. 40:219 (1981); and Nygren, J. Histochem. and Cytochem. 30:407 (1982).

The heteromultimers of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc., 1987).

Competitive binding assays rely on the ability of a labeled standard to compete with the test sample analyte for binding with a limited amount of heteromultimer. The amount of analyte in the test sample is inversely proportional to the amount of standard that becomes bound to the heteromultimer. To facilitate determining the amount of standard that becomes bound, the heteromultimers generally are insolubilized before or after the competition, so that the standard and analyte that are bound to the heteromultimers may conveniently be separated from the standard and analyte which remain unbound.

The heteromultimers are particularly useful for sandwich assays which involve the use of two molecules, each capable of binding to a different immunogenic portion, or epitope, of the sample to be detected. In a sandwich assay, the test sample analyte is bound by a first arm of the heteromultimer which is immobilized on a solid support, and thereafter a second arm of the heteromultimer binds to the analyte, thus forming an insoluble three part complex. See, e.g., U.S. Pat. No. 4,376,110. The second arm of the heteromultimer may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Below are examples of specific embodiments for carrying out the present invention. The examples are offered for illustrative purposes only, and are not intended to limit the scope of the present invention in any way.

All publications, patents and patent applications cited herein, whether supra or infra, are hereby incorporated by reference in their entirety.

EXAMPLES

A strategy is presented for preparing Fc-containing BsAb (FIG. 1C). In this strategy, we have engineered the $C_H3$ domain of antibody heavy chains so that they heterodimerize but do not homodimerize. This was accomplished by installing inter-chain disulfide bonds in the $C_H3$ domain in conjunction with sterically complimentary mutations obtained by rational design (Ridgway et al., supra (1996)) and phage display selection as described herein. Use of a single light chain for both antigen binding specificities circumvents the problem of light chain mispairing (FIG. 1A-1C). Antibodies with the same light chain were readily isolated by panning a very large human scFv library (Vaughan, T. J., et al., (1996) supra).

Example 1

Generation of Protuberance-Into-Cavity Heteromultimer Immunoadhesins

The $C_H3$ interface between the humanized anti-CD3/CD4-IgG chimera previously described by Chamow et al. J. Immunol. 153:4268 (1994) was engineered to maximize the percentage of heteromultimers which could be recovered. Protuberance-into-cavity and wild-type $C_H3$ variants were compared in their ability to direct the formation of a humanized antibody-immunoadhesin chimera (Ab/Ia) anti-CD3/CD4-IgG.

Thus, mutations were constructed in the $C_H3$ domain of the humanized anti-CD3 antibody heavy chain and in CD4-IgG by site-directed mutagenesis using mismatched oligonucleotides (Kunkel et al., Methods Enzymol. 154:367 (1987) and P. Carter, in Mutagenesis: a Practical Approach, M. J. McPherson, Ed., IRL Press, Oxford, UK, pp. 1-25 (1991)) and verified by dideoxynucleotide sequencing (Sanger et al., Proc. Natl. Acad. Sci. USA 74:5463 (1977)). See Table 3 below.

TABLE 3

| $C_H3$ of anti-CD3 | $C_H3$ of CD4-IgG |
|---|---|
| Most Preferred Mutants | |
| T366Y | Y407T |
| T366W | Y407A |
| F405A | T394W |
| Y407T | T366Y |
| T366Y:F405A | T394W:Y407T |
| T366W:F405W | T394S:Y407A |
| F405W:Y407A | T366W:T394S |
| Preferred Mutants | |
| F405W | T394S |

Residue T366 is within hydrogen-bonding distance of residue Y407 on the partner $C_H3$ domain. Indeed the principal intermolecular contact to residue T366 is to residue Y407 and vice versa. One protuberance-into-cavity pair was created by inverting these residues with the reciprocal mutations of T366Y in one $C_H3$ domain and Y407T in the partner domain thus maintaining the volume of side chains at the interface. Mutations are denoted by the wild-type residue followed by the position using the Kabat numbering system (Kabat et al. (1991) supra) and then the replacement residue in single-letter code. Multiple mutations are denoted by listing component single mutations separated by a colon.

Phagemids encoding anti-CD3 light (L) and heavy (H) chain variants (Shalaby et al., J. Exp. Med. 175:217 (1992) and Rodrigues et al., Int. J. Cancer (Suppl.) 7:45 (1992)) were co-transfected into human embryonic kidney cells, 293S, together with a CD4-IgG variant encoding phagemid (Byrn et al., Nature 344:667 (1990)) as previously described (Chamow et al., J. Immunol. 153:4268 (1994)). The total amount of transfected phagemid DNAs was fixed whereas the ratio of different DNAs was varied to maximize the yield of Ab/Ia chimera. The ratio (by mass) of Ia: heavy chain:light chain input DNAs (15 μg total) was varied as follows: 8:1:3; 7:1:3; 6:1:3; 5:1:3; 4:1:3; 3:1:3; 1:0:0; 0:1:3.

The products were affinity purified using Staphylococcal protein A (ProSep A, BioProcessing Ltd, UK) prior to analysis by SDS-PAGE followed by scanning LASER densitometry. Excess light over heavy chain DNA was used to avoid the light chain from being limiting. The identity of products was verified by electroblotting on to PVDF membrane (Matsudaira, J. Biol. Chem. 262:10035 (1987)) followed by amino terminal sequencing.

Co-transfection of phagemids for light chain together with those for heavy chain and Ia incorporating wild-type $C_H3$ resulted in a mixture of Ab/Ia chimera, IgG and Ia homodimer products as expected (Chamow et al., J. Immunol. 153:4268 (1994)). The larger the fraction of input DNA encoding antibody heavy plus light chains or Ia the higher the fraction of corresponding homodimers recovered. An input DNA ratio of 6:1:3 of Ia:H:L yielded 54.5% Ab/Ia chimera with similar fractions of Ia homodimer (22.5%) and IgG (23.0%). These ratios are in good agreement with those expected from equimolar expression of each chain followed by random assortment of heavy chains with no bias being introduced by the method of analysis: 50% Ab/Ia chimera, 25% Ia homodimer and 25% IgG.

In contrast to chains containing wild-type $C_H3$, Ab/Ia chimera was recovered in yields of up to 92% from cotransfections in which the anti-CD3 heavy chain and CD4-IgG Ia contained the Y407T cavity and T366Y protuberance mutations, respectively. Similar yields of antibody/immunoadhesin chimera were obtained if these reciprocal mutations were installed with the protuberance on the heavy chain and the cavity in the Ia. In both cases monomer was observed for the chain containing the protuberance but not the cavity. Without being limited to any one theory, it is believed that the T366Y protuberance is more disruptive to homodimer formation than the Y407T cavity. The fraction of Ab/Ia hybrid was not significantly changed by increasing the size of both protuberance and cavity (Ab T366W, Ia Y407A). A second protuberance and cavity pair (Ab F405A, Ia T394W) yielded up to 71% Ab/Ia chimera using a small fraction of Ia input DNA to offset the unanticipated proclivity of the Ia T394W protuberance variant to homodimerize. Combining the two independent protuberance-into-cavity mutant pairs (Ab T366Y:F405A, Ia T394W:Y407T) did not improve the yield of Ab/Ia hybrid over the Ab T366Y, Ia Y407T pair.

The fraction of Ab/Ia chimera obtained with T366Y and Y407T mutant pair was virtually independent of the ratio of input DNAs over the range tested. Furthermore the contaminating species were readily removed from the Ab/Ia chimera by ion exchange chromatography (0-300 mM NaCl in 20 mM Tris-HCl, pH 8.0) on a mono S HR 5/5 column (Pharmacia, Piscataway, N.J.). This augurs well for the preparation of larger quantities Ab/Ia chimeras using stable cell lines where the relative expression levels of Ab and Ia are less readily manipulated than in the transient expression system.

The protuberance-into-cavity mutations identified are anticipated to increase the potential applications of Fc-containing BsAb by reducing the complexity of the mixture of products obtained from a possible ten major species (Suresh et al., Methods Enzymol. 121:210 (1990)) down to four or less (FIGS. 1A-1B). It is expected that the T366Y and Y407T mutant pair will be useful for generating heteromultimers of other human IgG isotypes (such as $IgG_2$, $IgG_3$ or $IgG_4$) since T366 and Y407 are fully conserved and other residues at the $C_H3$ domain interface of $IgG_1$ are highly conserved.

Example 2

Generation of Non-Naturally Occurring Disulfide Linkages in Heteromultimeric Immunoadhesins A. Design of $C_H3$ Inter-Chain Disulfide Bonds.

Three criteria were used to identify pairs of residues for engineering a disulfide bond between partner $C_H3$ domains: i) The Cα separation preferably is similar to those found in natural disulfide bonds (5.0 to 6.8 Å) (Srinivasan, N., et al., Int. J. Peptides Protein Res. 36:147-155 (1990)). Distances of up to 7.6 Å were permitted to allow for main chain movement and to take into account the uncertainty of atomic positions in the low resolution crystal structure (Deisenhofer, Biochemistry 20:2361-2370 (1981)). ii) The Cα atoms should be on different residues on the two $C_H3$ domains. iii) The residues are positioned to permit disulfide bonding (Srinivasan, N., et al., (1990) supra).

B. Modeling of disulfide bonds. Disulfide bonds were modeled into the human $IgG_1$ Fc (Deisenhofer, supra) as described for humAb4D5-Fv (Rodrigues et al., Cancer Res. 55:63-70 (1995)) using Insight II release 95.0 (Biosym/MSI).

C. Construction of $C_H3$ variants. Mutations were introduced into the $C_H3$ domain of a humanized anti-CD3 heavy chain or CD4-IgG by site-directed mutagenesis (Kunkel, et al., Methods Enzymol. 154:367-382 (1987)) using the following synthetic oligonucleotides:

```
Y349C,
                                        (SEQ. ID NO: 1)
5' CTCTTCCCGAGATGGGGGCAGGGTGCACACCTGTGG 3'

S354C,
                                        (SEQ. ID NO: 2)
5' CTCTTCCCGACATGGGGGCAG 3'

E356C,
                                        (SEQ. ID NO: 3)
5' GGTCATCTCACACCGGGATGG 3'

E357C,
                                        (SEQ. ID NO: 4)
5' CTTGGTCATACATTCACGGGATGG 3'

L351C,
                                        (SEQ. ID NO: 5)
5' CTCTTCCCGAGATGGGGGACAGGTGTACAC 3'

D399C,
                                        (SEQ. ID NO: 6)
5' GCCGTCGGAACACAGCACGGG 3'

K392C,
                                        (SEQ. ID NO: 7)
5' CTGGGAGTCTAGAACGGGAGGCGTGGTACAGTAGTTGTT 3'

T394C,
                                        (SEQ. ID NO: 8)
5' GTCGGAGTCTAGAACGGGAGGACAGGTCTTGTA 3'

V397C,
                                        (SEQ. ID NO: 9)
5' GTCGGAGTCTAGACAGGGAGG 3'

D399S,
                                        (SEQ. ID NO: 10)
5' GCCGTCGGAGCTCAGCACGGG 3'

K392S,
                                        (SEQ. ID NO: 11)
5' GGGAGGCGTGGTGCTGTAGTTGTT 3'

C231S: C234S
                                        (SEQ. ID NO: 12)
5' GTTCAGGTGCTGGGCTCGGTGGGCTTGTGTGAGTTTTG 3'
```

Mutations are denoted by the amino acid residue and number (Eu numbering scheme of Kabat et al., supra (1991)), followed by the replacement amino acid. Multiple mutations are represented by the single mutation separated by a colon. Mutants were verified by dideoxynucleotide sequencing (Sanger et al., supra (1977)) using Sequenase version 2.0 (United States Biochemicals, Cleveland, Ohio).

D. An inter-chain disulfide enhances heterodimer formation. Six pairs of molecules containing inter-chain disulfide bonds in the $C_H3$ domain ("disulfide-$C_H3$" variants; v1-v6, Table 4) were compared with parent molecules in their ability to direct the formation of an Ab/Ia hybrid, anti-CD3/CD4-IgG (Chamow et al., supra (1994)). Plasmids encoding CD4-IgG and anti-CD3 heavy chain variants were co-transfected into 293S cells, along with an excess of plasmid encoding the anti-CD3 light chain. The yield of heterodimer was optimized by transfecting with a range of Ia:H chain:L chain DNA ratios. The Ab/Ia heterodimer, IgG and Ia homodimer products were affinity-purified using Staphylococcal protein A and quantified by SDS-PAGE and scanning laser densitometry (Ridgway et al., supra (1996)).

Each disulfide-$C_H3$ pair gave rise to three major species, similar to the parent molecules. However, Ab/Ia heterodimer from disulfide-$C_H3$ variants was shifted in electrophoretic mobility, consistant with formation of an inter-chain disulfide in the $C_H3$ domain. Further evidence of disulfide bond formation was provided by the inter-chain disulfides in the hinge. Covalently bonded Ab/Ia hybrids were observed by SDS-PAGE for disulfide-$C_H3$ variants but not for molecules with wildtype $C_H3$ domains in which hinge cysteines were mutated to serine. Disulfide-$C_H3$ variants were prepared and designated Y349C/S354° C., Y349C/E356° C., Y349C/E357° C., L351C/E354° C., T394C/E397° C., and D399C/K392C. Only one variant (D399C/K392° C.) substantially increased the yield of Ab/Ia hybrid over wildtype (76% vs. 52%, respectively) as determined by SDS-PAGE analysis of the variants. Mutations are denoted by the amino acid residue and number (Eu numbering scheme of Kabat et al. (1991) supra), followed by the replacement amino acid. Mutations in the first and second copies of $C_H3$ come before and after the slash, respectively. Residues in the second copy of $C_H3$ are designated with a prime ('). This improvement apparently reflects disulfide bond formation rather than replacement of residues K392 and D399, since the mutations K392S/D399'S gave both a similar Ab/Ia yield and Ab/Ia electrophoretic mobility relative to wildtype. Homodimers migrated similarly to those with wildtype Fc domains, demonstrating preferential engineered inter-chain disulfide bond formation in the $C_H3$ domain of heterodimers. All disulfide-C variants were expressed at approximately the same level as the parent molecules in 293S cells.

E. Disulfides combined with protuberance-into-cavity engineering increases the yield of heterodimer to 95%. The best disulfide pair increased the percent of heterodimer to 76% and the protuberance-into-cavity strategy increased the percent of heterodimer to 87% (Table 4; see also Ridgway et al., (1996) supra). These two strategies rely on different principles to increase the probability of generating heterodimer. Therefore, we combined the two strategies, anticipating further improvement in the yield of heterodimer. Two of the modeled disulfides, containing L351C or T394C, could potentially form disulfide-bonded homodimers as well as disulfide-bonded heterodimers (L351C/S354° C. and T394C/V397° C.), thus decreasing their utility. The remaining four disulfide pairs were installed into the phage-selected heterodimer (variants v9-v16) and assayed for the yield of heterodimer (Table 4). Yields of approximately 95% heterodimer were obtained. Again, the heterodimer showed an electrophoretic mobility shift compared to wildtype and v8 variants.

of cavity mutants was created in this second copy of $C_H3$ by randomization of the closest neighboring residues to the protuberance on the first $C_H3$ domain. Phage displaying stable $C_H3$ heterodimers were then captured using an anti-flag Ab.

A $C_H3$ phage display library of $1.1 \times 10^5$ independent clones was constructed by replacement of a segment of the natural $C_H3$ gene with a PCR fragment. The fragment was obtained by PCR amplification using degenerate primers to randomize positions 366, 368 and 407 using standard techniques.

After 2 to 5 rounds of selection, the fraction of full length clones was 90%, 60%, 50% and 10%, respectively, as judged by agarose gel electrophoresis of single-stranded DNA. Phagemids containing full length clones were gel-purified after 5 rounds of selection. Two thousand transformants were obtained after retransforming XL1-BLUE™ cells (Stratagene).

A mean of >$10^6$ copies of each clone was used per round of panning. Thus, numerous copies of each clone in the library

TABLE 4

Yields of Heterodimers from $C_H3$ Variants

| Variant | Mutations | | Yield of heterodimer |
| --- | --- | --- | --- |
| | Subunit A | Subunit B | (%) |
| wildtype | — | — | 51 ± 1 |
| v1 | Y349C | S354C | 54 ± 4 |
| v2 | Y349C | E356C | 55 ± 6 |
| v3 | Y349C | E357C | 57 ± 4 |
| v4 | L351C | E354C | 56 ± 3 |
| v5 | T394C | E397C | 57 ± 2 |
| v6 | D399C | K392C | 73 ± 3 |
| v7 | D399S | L392S | 55 ± 1 |
| v8 | T366W | T366S: L368A: Y407V | 86.7 ± 2.3 |
| v9 | T366W: D399C | T366S: L368A: K392C: Y407V | 86.5 ± 0.5 |
| v11 | S354C: T366W | Y349C: T366S: L368A: Y407V | 95 ± 2 |
| v12 | E356C: T366W | Y349C: T366S: L368A: Y407V | 94 ± 2 |
| v13 | E357C: T366W | Y349C: T366S: L368A: Y407V | 93 ± 2 |
| v14 | T366W: K392C | T366S: D399C: L368A: Y407V | 92 ± 1 |
| v15 | Y349C: T366W | S354C: T366S: L368A: Y407V | 90 ± 1 |
| v16 | Y349C: T366W | E356C: T366S: L368A: Y407V | 95.5 ± 0.5 |
| v17 | Y349C: T366W | E357C: T366S: L368A: Y407V | 91.0 ± 1.0 |

Example 3

Structure-Guided Phage Display Selection for Complementary Mutations that Enhance Protein-Protein Interaction in Heteromultimers The following strategy is useful in the selection of complementary mutations in polypeptides that interact at an interface via a multimerization domain. The strategy is illustrated below as it applies to the selection of complementary protuberance-into-cavity mutations. However, the example is not meant to be limiting and the strategy may be similarly applied to the selection of mutations appropriate for the formation of non-naturally occurring disulfide bonds, leucine zipper motifs, hydrophobic interactions, hydrophilic interactions, and the like.

A. Phage display selection. A phage display strategy was developed for the selection of stable $C_H3$ heterodimers and is diagrammed in FIG. 2. The selection uses a protuberance mutant, T366W (Ridgway et al., supra (1996)), fused to a peptide flag (gD peptide flag, for example, Lasky, L. A. and Dowbenko, D. J. (1984) DNA 3:23-29; and Berman, P. W., et al. (1985) Science 227:1490-1492) that is coexpressed with a second copy of $C_H3$ fused to M13 gene III protein. A library were likely available for selection, even though some deletion mutants arose during panning.

After 7 rounds of panning, the $C_H3$ mutants obtained approached a consensus amino acid sequence at the randomized residues. Virtually all clones had serine or threonine at residue 366 indicating a very strong preference for a β-hydroxyl at this position. A strong preference for hydrophobic residues was observed for residues 368 and 407, with valine and alanine predominating. Six different amino acid combinations were recovered at least twice, including the triple mutant, T366S:L368A:Y407V, which was recovered 11 times. None of these phage selectants has an identical sequence to a previously designed heterodimer, T366W/Y407'A (Ridgway, J. B. B., et al., (1996), supra. The phage selectants may be less tightly packed than the wild-type $C_H3$ homodimer as judged by a 40-80 Å$^3$ reduction in total side chain volume of the domain interface residues.

$C_H3$ variants encoded on the expression plasmid pAK19 (Carter et al. 1992) were introduced into E. coli strain 33B6, expressed, and secreted from E. coli grown to high cell density in a fermentor. The T366S:L368A:Y407V mutant purified by DEAE-Sepharose FF, ABx and Resource S chromatography gave a single major band following SDS-PAGE. Other $C_H3$ variants were recovered with similar purity. The molecular masses of wild-type $C_H3$ and T366S:L368A: Y407V, T366W and Y407A variants determined by high resolution electrospray mass spectrometry were as expected.

B. Phage-selected heterodimer stability. The stability of $C_H3$ heterodimers was first assessed by titrating corresponding phage with guanidine hydrochloride, followed by dilution and quantification of residual heterodimer by enzyme-linked immunosorbent assay (ELISA). The guanidine hydrochloride denaturation assay with $C_H3$-phage provides a means to screen selectants rapidly.

Phage were prepared from individual clones following 7 rounds of selection and also from the control vector, pRA1. Briefly, phagemids in XL1-BLUE™ were used to inoculate 25 ml LB broth containing 50 µg/ml carbenicillin and 10 µg/ml tetracycline in the presence of $10^9$ pfu/ml M13K07 and incubated overnight at 37° C. The cells were pelleted by centrifugation (6000 g, 10 min, 4° C.). Phage were recovered from the supernatant by precipitation with 5 ml 20% (w/v) PEG, 2.5 M NaCl followed by centrifugation (12000 g, 10 min, 4° C.) and then resuspended in 1 ml PBS. 180 µl 0-6 M guanidine hydrochloride in PBS was added to 20 µl phage preparations and incubated for 5.0 min at approximately ~25° C. Aliquots (20 µl) of each phage sample were then diluted 10-fold with water. The presence of $C_H3$ heterodimer was assayed by ELISA using 5B6-coated plates and detecting the phage with an anti-M13 polyclonal Ab conjugated to horseradish peroxidase, using o-phenylenediamine as the substrate. The reaction was quenched by the addition of 50 µl 2.5 M $H_2SO_4$ and the absorbance measured at 492 nm. The absorbance data were plotted against the guanidine hydrochloride concentration during the melt and fitted to a 4 parameter model by a non-linear least squares method using Kaleidagraph 3.0.5 (Synergy Software).

The most frequently recovered heterodimer, T366W/ T366'S:L368'A:Y407'V, is similar in stability to other phage-selected heterodimers. This phage-selected heterodimer is significantly more stable than the designed heterodimer, T366W/Y407'A but less stable than the wild-type $C_H3$. All $C_H3$ variants, both individually and in combination, were found to be dimers by size exclusion chromatography under the conditions that these same molecules were studied by calorimetry (1.75 mg/ml, in phosphate-buffered saline (PBS)). The only exception was the T366S:L368A:Y407V mutant alone which had a slightly shorter retention time than $C_H3$ dimers.

A 1:1 mixture of T366W, protuberance, and T366S: L368A:Y407V, cavity, mutants melts with a single transition at 69.4° C., consistent with subunit exchange and formation of a stable heterodimer. In contrast, the T366W protuberance homodimer is much less stable than the T366W/T366'S: L368'A:Y407'V protuberance-into-cavity heterodimer ($\Delta T_m$=-15.0° C.). The T366S:L368A:Y407V cavity mutant on its own is prone to aggregate upon heating and does not undergo a smooth melting transition.

The designed cavity mutant, Y407A, melts at 58.8° C. and 65.4° C. in the absence and presence of the T366W protuberance mutant, respectively. This is consistent with subunit exchange and formation of a T366W/Y407'A heterodimer that has greater stability than either T366W ($\Delta T_m$=11.0° C.) or Y407A ($\Delta T_m$=6.6° C.) homodimers. The phage-selected heterodimer, T366W/T366'S:L368'A:Y407'V, is more stable than the designed heterodimer, T366W/Y407'A, ($\Delta T_m$=4.0° C.), but is less stable than the wild-type $C_H3$ homodimer ($\Delta T_m$=-11.0° C.).

Figure 3A:
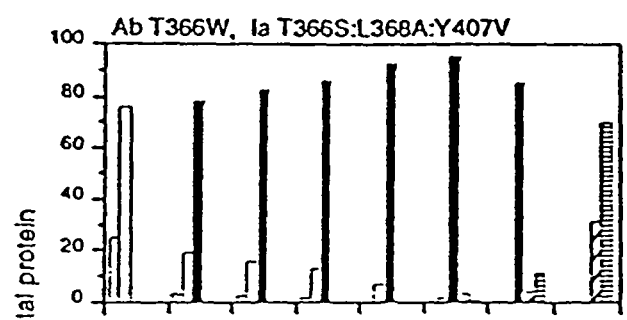
FIGS. 3A-3C.
Figure 3B:
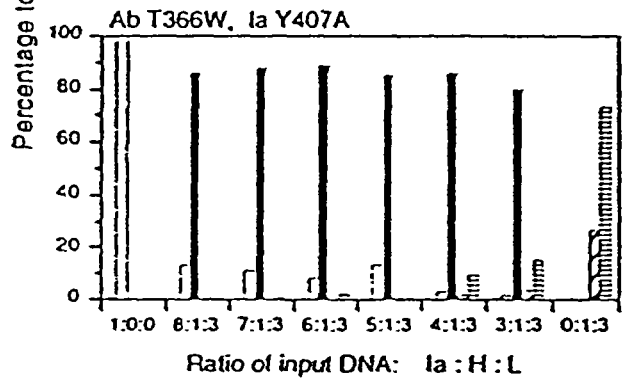
Figure 3C:
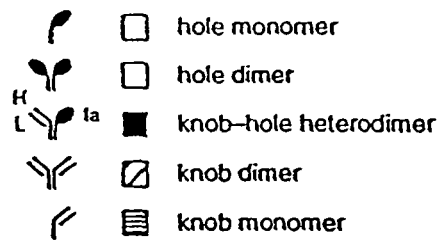

C. Multimerization of a phage-selected antibody immunoadhesin (Ab/Ia) in vivo. Phage-selected and designed $C_H3$ mutants were compared in their ability to direct the formation of an Ab/Ia hybrid, anti-CD3/CD4-IgG in vivo (Chamow et al., (1994), supra. This was accomplished by coexpression of humanized anti-CD3 light (L) and heavy chains together with CD4-IgG. Formation of heterodimers and homodimers was assessed by protein A purification followed by SDS-PAGE and scanning laser densitometry (Ridgway, et al., (1996), supra). Comparable yields of Ab/Ia hybrid were recovered from cotransfections in which the anti-CD3 heavy chain contained the designed protuberance mutation, T366W, and the Ia contained either the phage-selected mutations, T366S: L368A:Y407V, or designed cavity mutation, Y407A (FIG. 3).

Phage-selected and designed $C_H3$ mutants were next evaluated in their propensity to form homodimers. The protuberance mutation, T366W, is apparently very disruptive to homodimerization since cotransfection of corresponding antibody heavy and light chains leads to an excess of HL monomers (may include non disulfide-bonded IgG) over IgG. In contrast, IgG but no HL monomers are observed for the same antibody containing wild-type $C_H3$ domains. The cavity mutations, T366S:L368A:Y407V, are somewhat disruptive to homodimerization since transfection of the corresponding phagemid leads to a mixture of predominantly Ia dimers with some Ia monomers. The cavity mutation, Y407A, is minimally disruptive to homodimerization as judged by the presence of Ia dimers but no Ia monomers following transfection of the corresponding phagemid.

The phage display selection strategy described herein allows the selection in favor of $C_H3$ mutants that form stable heterodimers and selection against mutants that form stable homodimers. The counter selection against homodimers occurs because "free" $C_H3$ mutants will compete with the flagged $C_H3$ knob mutant for binding to available $C_H3$ mutant-gene III fusion protein. The free $C3_H$ mutants arise as a result of the amber mutation between the natural $C_H3$ gene and M13 gene III. In an amber suppressor host such as XL1-Blue, both $C_H3$-gene III fusion protein and corresponding free $C_H3$ will be secreted.

Guanidine hydrochloride denaturation proved to be a useful tool for the preliminary screening of the stability of $C_H3$ heterodimers on phage. Phage maintain infectivity for *E. coli* even after exposure to 5 M guanidine hydrochloride (Figini et al., J. Mol. Biol. 239:68-78 (1994)). Thus, guanidine may also be useful to increase the stringency of mutant selection.

Rational design and screening of phage display libraries are complementary approaches to remodeling a domain interface of a homodimer to promote heterodimerization. In the case of $C_H3$ domains, designed mutants identified domain interface residues that could be recruited to promote heterodimerization. Phage display was then used here to search permutations of 3 residues neighboring a fixed protuberance for combinations that most efficiently form heterodimers. Phage selectants are useful to facilitate further rational redesign of the domain interface, while the phage selection strategy described herein demonstrates its usefulness for remodeling protein-protein interfaces.

Example 4

Generation and Assembly of Heteromultimeric Antibodies or Antibody/Immunoadhesins Having Common Light Chains The following example demonstrates preparation of a heteromultimeric bispecific antibody sharing the same light chain according to the invention and the ability of that antibody to bind its target antigens.

A. Identification of Antibodies that Share the Same Light Chain: Comparison of Antibody Libraries Raised to Eleven Antigens.

A large human single chain Fv (scFv) antibody library (Vaughan et al. (1996), supra) was panned for antibodies specific for eleven antigens including Axl(human receptor tyrosine kinase ECD), GCSF-R (human granulocyte colony stimulating factor receptor ECD), IgE (murine IgE), IgE-R (human IgE receptor α-chain), MPL (human thrombopoietin receptor tyrosine kinase ECD), MusK (human muscle specific receptor tyrosine kinase ECD), NpoR (human orphan receptor NpoR ECD), Rse (human receptor tyrosine kinase, Rse, ECD), HER3 (human receptor tyrosine kinase HER3/c-erbB3 ECD), Ob-R (human leptin receptor ECD), and VEGF (human vascular endothelial growth factor) where ECD refers to the extracellular domain. The nucleotide sequence data for scFv fragments from populations of antibodies raised to each antigen was translated to derive corresponding protein sequences. The $V_L$ sequences were then compared using the program "align" with the algorithm of Feng and Doolittle (1985, 1987, 1990) to calculate the percentage identity between all pairwise combinations of chains (Feng, D. F. and Doolittle, R. F. (1985) J. Mol. Evol. 21:112-123; Feng, D. F. and Doolittle, R. F. (1987) J. Mol. Evol. 25:351-360; and Feng, D. F. and Doolittle, R. F. (1990) Methods Enzymol. 183:375-387). The percent sequence identity results of each pairwise light chain amino acid sequence comparison were arranged in matrix format (see Appendix).

For most pairwise comparisons, at least one common light chain sequence was found. Table 5 is a comparison of the $V_L$ chains showing the frequencies of scFv sharing identical light chains (100% identity) determined by alignment of 117 $V_L$ amino acid sequences. For example, the entry 4/9 (HER3×Ob-R, highlighted in a black box), denotes that 4 clones that bind HER3 were found to share their $V_L$ sequence with one or more anti-Ob-R clones, whereas 9 clones binding the Ob-R share their $V_L$ sequence with one or more anti-HER3 clones. The entries on the diagonal represent the number of antibody clones within a population that share a $V_L$ sequence with one or more clones in the population. For example, examination of the MPL clones revealed 5 clones that shared their $V_L$ sequence with one or more other MPL clones. In the cases where no common light chain sequence was observed, such as for (IgE×Axl) or (NpoR×IgE-R), the number of fragments compared for at least one specificity was very small (5 or less). Given the number of common light chains found, it is likely that common light chains can be found for any $V_L$ comparison if a sufficient number of clones are compared.

The amino acid sequences of light chains were examined for the positions of amino acid residue differences when the sequence identity relative to a chosen common light chain was 98% and 99%. FIG. 4 is a comparison of $V_L$ sequences of eight different antibodies with specificities for Axl (clone Axl.78), Rse (clones Rse.23, Rse.04, Rse.20, and Rse.15), IgER (clone IgER.MAT2C1G11), Ob-R (clone obr.4), and VEGF (clone vegf.5). The position of the antigen binding CDR residues according to a sequence definition (Kabat, G. A., et al. (1991) supra) or structural definition (Chothia and Lesk, (1987) J. Mol. Biol. 196:901-917) are shown by underlining and #, respectively. Light chain residues that differ from the Axl.78 sequence are shown by double underlining. Of the 9 light chains compared, 6 are identical. The light chains of Rse.04 and obr.4 (approximately 99% sequence identity) differ by one residue outside of the antigen binding CDRs. The light chain of Rse.20 (approximately 98% sequence identity) differs by two residues outside of the antigen binding CDRs. The amino acid residue changes may have little or no affect on antigen binding. Thus, the sequence similarity of these light chains makes them candidates for the common light chain of the invention. Alternatively, according to the invention, such light chains having 98-99% sequence identity with the light chain of a prospective paired scFv (Axl.78, for example) may be substituted with the paired light chain and retain binding specificity.

B. Identification of Antibodies that Share the Same Light Chain and Construction of a Bispecific Antibody Sharing that Light Chain: Anti-Ob-R/Anti-HER3.

ScFv fragments that bound human leptin receptor (Ob-R) or the extracellular domain of the HER3/c-erbB3 gene product (HER3) were obtained by three rounds of panning using a large human scFv phage library (Vaughan et al. (1996), supra). Leptin receptor-IgG and HER3-IgG (10 μg in 1 ml PBS were used to coat separate Immunotubes (Nunc; Maxisorp) overnight at 4° C. Panning and phage rescue were then performed as described by Vaughan et al. (1996), supra, with the following modifications. A humanized antibody, huMAb4D5-8 (Carter, P. et al. (1992) PNAS USA 89:4285-4289) or humanized anti-IgE (Presta, L. et al. (1993) J. Immunol. 151:2623-2632) at a concentration of 1 mg/ml was included in each panning step to absorb Fc-binding phage. In addition, panning in solution (Hawkins, R. E., et al. (1992) J. Mol. Biol. 226:889-896) was also used to identify scFv binding leptin receptor. The leptin receptor was separated from the Fc by site-specific proteolysis of leptin receptor-IgG with the engineered protease, Genenase (Carter, P., et al. (1989) Proteins: Structure, Function and Genetics 6:240-248) followed by protein A Sepharose chromatography. The leptin receptor was biotinylated and used at a concentration of 100 nM, 25 nM and 5 nM for the first, second, and third rounds of panning, respectively. Phage binding biotinylated antigen were captured using streptavidin-coated paramagnetic beads (Dynabeads, Dynal, Oslo, Norway).

Clones from rounds 2 and 3 of each panning were screened by phage and scFv ELISA using the corresponding antigen and also a control immunoadhesin or antibody. The diversity of antigen-positive clones was analyzed by PCR-amplification of the scFv insert using the primers, fdtetseq and PUC reverse (Vaughan et al. (1996), supra) and by digestion with BstNI (Marks et al. (1991) supra). One to five clones per BstNI fingerprint were then cycle-sequenced using fluorescent dideoxy chain terminators (Applied Biosystems) using PCR heavy link and myc seq 10 primers (Vaughan et al. (1996), supra). Samples were analyzed using an Applied Biosystems Automated DNA Sequencer and sequences analyzed using SeqEd. It is also noted that the guanidine hydrochloride antibody denaturation and in vitro chain shuffling method of Figini combined with phage display selection is useful as a method of selecting antibodies having the same light chain (Figini, M. et al. (1994), supra, herein incorporated by reference in its entirety).

Using the method described above, eleven different anti-HER3 clones and 18 anti-Ob-R clones (11 form panning using coated antigen and 7 from panning with biotinylated antigen) were obtained. The clones were sequenced by standard techniques to determine the sequences of the light chains associated with each binding domain (FIG. 5). The sequences are the $V_H$ and common $V_L$ sequences of the anti-Ob-R clone 26 and anti-HER3 clone 18 used to construct a bispecific antibody (see below). The residues are numbered according to (Kabat, E. A., et al. (1991) supra). The position of the antigen binding CDR residues according to a sequence definition (Kabat et al. (1991) supra) or structural definition (Chothia and Lesk, (1987) J. Mol. Biol. (1987) 196:901-917)

are shown by underlining and overlining, respectively. Identity between residues in the $V_H$ sequences is indicated by *.

The sequences of the light chains were compared for multiple anti-HER3 clones relative to multiple anti-Ob-R clones (FIG. 8 and Table 5). It was observed that four out of eleven anti-HER3 clones share identical $V_L$ with one or more anti-Ob-R receptor clones. Conversely, nine out of eighteen anti-Ob-R clones share the same $V_L$ as one of the anti-HER3 clones (See Table 5, blackened box).

TABLE 5

Shared $V_L$ usage by scFv against different target antigens

| Antigen Specificity | # scFv | Axl | GCSF-R | IgE | IgE-R | MPL | MusK | NpoR | Rse | HER3 | Ob-R | VEGF |
|---|---|---|---|---|---|---|---|---|---|---|---|---|
| Axl | 12 | 2 | 2/2 | 0/0 | 1/1 | 2/3 | 1/1 | 0/0 | 3/5 | 2/2 | 2/5 | 1/1 |
| GCSF-R | 11 | | 0 | 1/1 | 2/2 | 2/3 | 1/1 | 2/2 | 2/3 | 2/2 | 3/3 | 2/3 |
| IgE | 2 | | | 0 | 1/1 | 1/1 | 0/0 | 1/1 | 1/1 | 1/1 | 1/1 | 0/0 |
| IgE-R | 4 | | | | 0 | 1/1 | 0/0 | 1/1 | 2/3 | 1/1 | 1/1 | 1/1 |
| MPL | 23 | | | | | 5 | 5/3 | 3/2 | 5/8 | 7/5 | 5/9 | 2/2 |
| MusK | 3 | | | | | | 0 | 1/1 | 1/2 | 2/2 | 1/1 | 1/2 |
| NpoR | 5 | | | | | | | 0 | 1/1 | 2/2 | 2/2 | 1/2 |
| Rse | 20 | | | | | | | | 7 | 7/4 | 5/8 | 2/1 |
| HER3 | 11 | | | | | | | | | 3 | ▨ | 4/4 |
| Ob-R | 18 | | | | | | | | | | 7 | 1/2 |
| VEGF | 8 | | | | | | | | | | | 2 |

Construction of anti-Ob-R/anti-HER3, a bispecific antibody having a common light chain was performed as follows. Altered $C_H3$ first and second polypeptides having the complementary protuberances and cavities as well as the non-naturally occurring disulfide bonds between the first and second polypeptides were used in the construction of a Fc-containing bispecific antibody. The $V_L$ from anti-Ob-R clone #26 and anti-HER3 clone #18, which clones share the same light chain, as well as the heavy chains from each antibody were used to prepare the bispecific antibody according to the procedures disclosed herein.

This antibody had an electrophoretic mobility shift in apparent molecular weight relative to a bispecific antibody that differed only by a lack of alterations for generating non-natural disulfide bonds. An 8% SDS-PAGE gel of heterodimeric antibody variants with and without non-naturally occurring disulfide bonds showed a mobility shift from approximately 230 apparent MW for wild type heterodimer to approximately 200 apparent MW for a heterodimer having one non-natural disulfide bond. The MW shift was sufficient to allow determination of the percent of each variant that successfully formed the non-natural disulfide bond.

The binding specificity for both Ob-R and for HER3 of the bispecific antibody is tested by standard ELISA procedures such as the following method. Ob-R binding is demonstrated in an ELISA assay with Ob-R present as an Ob-R-Ig fusion protein. The Ob-R-Ig fusion protein is coated onto the well of a 96-well microtitre plate and the bispecific antibody is added.

The well is washed several times to eliminate non-specific binding to Ob-R-Ig. As a second component in the same assay, a biotinylated HER3-Ig fusion protein is added and detected by means of streptavidin-horseradish peroxidase complex binding to the biotinylated HER3-Ig fusion protein. Binding is detected by generation of a color change upon addition of hydrogen peroxide and TMB peroxidase substrate (Kirkegaard and Perry Laboratories, Gaithersburg, Md.).

Under the conditions just described, the binding of a bispecific antibody to both Ob-R-Ig and to HER3-Ig would be observed as detectable label immobilized on the surface of the microtitre well due to the formation of a complex comprising immobilized Ob-R-Ig/bispecific antibody/HER3-Ig biotin/detectably labeled streptavidin. Antibodies that bind Ob-R-Ig, but not HER3-Ig, do not form the above complex, providing a negative result. Similarly, antibodies that bind to HER3-Ig, but not Ob-R-Ig, do not form the above complex and provide a negative result. In contrast, the bispecific antibody expected to bind both Ob-R-Ig and HER3-Ig, forms the complex yielding a positive result in the assay, demonstrating that the bispecific antibody, having a common light chain, binds both HER3 and Ob-R.

Expression and purification of the anti-(Ob-R/HER3) bispecific antibody was performed as follows. Human embryonic kidney 293S cells were transfected with three plasmid DNAs each separately encoding anti-Ob-R heavy chain, anti-HER3 heavy chain, or the light chain from clone 26 or 18 that was common to each of the antibodies, as described supra. For each transfection, the ratio of heavy chain-encoding DNA to light chain-encoding DNA was 1:3 so that light chain would not be limiting for assembly of anti-Ob-R/anti-HER3 bispecific antibody. Both heavy chains were transfected in a 1:1 ratio with respect to each other. 12 μg of total plasmid DNA was then co-transfected into 293S cells by means of calcium phosphate precipitation (Gorman, C., DNA Cloning, Vol. II, D. M. Glover, ed., IRL Press, Oxford, p. 143 (1985)). The cells were washed with PBS prior to adding growth media intended to enhance protein expression. Fc-containing proteins were purified from cell supernatants using immobilized protein A (ProSep A, BioProcessing Ltd., UK) and buffer-exchanged into PBS. Iodoacetamide was added to protein preparations to a final concentration of 50 mM to prevent reshuffling of disulfide bonds.

As an additional example, expression and purification of an anti-(CD3/CD4) antibody/immunoadhesin was performed as follows. Human embryonic kidney 293S cells were transfected with three plasmid DNAs, each plasmid separately encoding anti-CD3 light chain, anti-CD3 $IgG_1$ heavy chain, or anti-CD4 $IgG_1$ immunoadhesin. For each transfection, the ratio of light chain-encoding DNA to heavy chain-encoding DNA was 3:1 so that light-chain would not be limiting for assembly of anti-CD3 IgG. Additionally, because the immunoadhesin is poorly expressed, the ratio of immunoadhesin encoding plasmid was added in excess to heavy chain encoding plasmid. The ratios tested ranged from 3:1:3 through 8:1:3 for immunoadhesin:heavy chain:light chain phagemids. 10 μg total plasmid DNA were then co-transfected into 293S cells by means of calcium phosphate precipitation (Gorman, C. (1985), supra), washing cells with PBS prior to transfection. Fc-containing proteins were purified from cell supernatants using immobilized protein A (ProSep A, BioProcessing Ltd., UK) and buffer-exchanged into PBS. Iodoacetamide was added to protein preparations to a final concentration of 50 mM to prevent reshuffling of disulfide bonds.

In each of the above preparations, protein samples were electrophoresed on 8% polyacrylamide gels (Novex) and visualized by staining with Serva blue. Gels were de-stained leaving a faint background in an effort to allow visualization and quantitation of minor contaminants. Dried gels were scanned with the scanning densitometer (GS-670, BioRad) and protein products were quantitated with Molecular Analyst software.

Non-natural (engineered) disulfide bonds introduced into the $C_H3$ domain has been disclosed herein to enhance heterodimer formation. One pair of polypeptides, K392C/D399° C., enhanced heterodimer formation by generating up to 76% heterodimer (Table 4, variant v6). Moreover, when the presence of an inter-chain disulfide bond was combined with the protuberance-into-cavity technology, approximately 95% heterodimer was obtained (Table 4 variants v11, v12, and v16). Thus, the method of the invention of increasing specific protein/protein interaction between the first and second polypeptides of a bispecific antibody increases the yield of desired heteromultimer and minimizes the formation of undesired heteromultimers or homomultimers.

In addition, the method of characterizing the product heteromultimers by electrophoretic mobility analysis allows for the determination of the relative amount of desired heteromultimers relative to undesired products.

Selection of a common light chain as described herein further increases yield of the desired heteromultimer by eliminating the possibility of mispairing between variable heavy chains and light chains of a multispecific antibody.

C. Identification of Antibodies that Share the Same Light Chain and Construction of a Bispecific Antibody Sharing that Light Chain: Anti-Mpl/Anti-HER3.

Identification, construction and expression of another bispecific antibody of the invention is demonstrated herein. The methods described in Parts A and B of this example were utilized for the preparation of the anti-Mpl/anti-HER3 bispecific antibody.

Using the methods described in Section A of this example (Comparison of antibody libraries raised to eleven antigens), supra, the $V_H$ and $V_L$ amino acid sequences of the anti-HER3 scfv were compared with 23 scFv that bind to the human thrombopoietin receptor, c-Mpl. Five of the eleven anti-HER3 clones share an identical $V_L$ amino acid sequence with one or more Mpl-binding clones. Conversely, seven out of twenty-three anti-Mpl scFv shared the same $V_L$ as one of the anti-HER3 clones (see Table 5, supra, open box). In contrast, the $V_H$ amino acid sequences were much more diverse, with an identity level of 40 to 90% between any anti-Mpl and anti-HER3 clone.

The anti-Mpl scFv, 12B5 (Genbank accession number AF048775; SEQ ID NO:27, disclosed in U.S. application Ser. No. 08/918,148, hereby incorporated by reference in its entirety) and anti HER3 scFv clone H6 (Genbank accession number AF048774; SEQ ID NO:28) utilize identical $V_L$ sequences and substantially different $V_H$ sequences. These scFv fragments were used to construct the anti-Mpl/anti-HER3 bispecific IgG antibody capable of efficient heterodimerization due to the shared light chain as well as through the use of knobs-into-holes mutations (described herein) and an engineered disulfide bond between the $C_H3$ domains. Antibodies that share the same L chain were chosen to circumvent the problem of L chains pairing with non-cognate H chains. Two naturally occurring hinge region disulfide bonds were also present. The common L chain was cotransfected with the two H chains containing the $C_H3$ mutations from variant v11. The IgG products were purified by protein A affinity chromatography and analyzed by SDS-PAGE using standard techniques.

The bispecific IgG antibody (BsIgG) preparation gave rise to a single major band showing greater mobility than IgG containing wild-type $C_H3$ domains. This increase in electrophoretic mobility was consistent with the formation of the engineered disulfide bond in the BsIgG forming a more compact protein species.

The ability of the engineered anti-Mpl/anti-HER3 BsIgG antibody to bind both Mpl and HER3 ECD antigens was assessed using an ELISA as follows. Using PBS buffer in all steps, individual wells of a 96 well plate (Maxisorp, Nunc) were coated overnight with HER3-IgG or Mpl-IgG at 5 μg/ml, washed and then blocked for 1 hour with 0.5% (w/v) BSA. The primary antibodies were the anti-Mpl×anti-HER3 BsIgG containing the mutations, Y349C:T366S:L368A: Y407V/T366'W:S354° C., and corresponding parental anti-Mpl or anti-HER3 IgG with mutated Fc regions. The primary antibodies (1 μg/mL) were individually incubated at 2 h at 23° C. with biotinylated HER3-IgG and a 1:5000 dilution of streptavidin-horse radish peroxidase conjugate (Boehringer Mannheim) and then added to the wells and incubated for an additional 1 h at 23° C. Peroxidase activity was detected with TMB reagents as directed by the vendor (Kirkegaard and Perry Laboratories, Inc., Gaithersburg, Md.).

Figure 6:
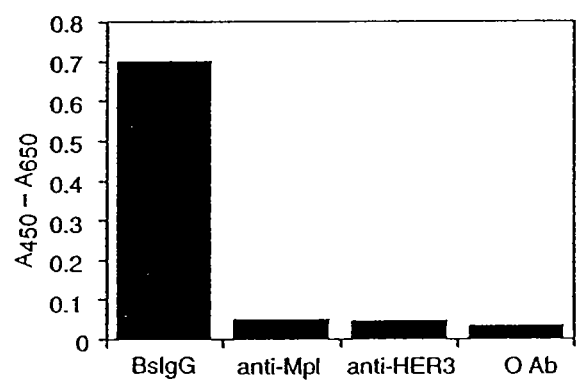
FIG. 6. Sandwich ELISA for detection of simultaneous binding to Mpl-IgG and HER3-IgG. Antibodies tested were the anti-Mpl×anti-HER3 BsIgG containing the mutations, Y349C:T366S:L368A:Y407V/T366'W:S354° C., together with corresponding parental anti-Mpl or anti-HER3 IgG with mutated Fc regions.

As anticipated, the anti-Mpl/anti-HER3 BsIgG bound efficiently and simultaneously to each Mpl and HER3 ECD antigens individually as well as to both antigens simultaneously. By contrast, the parental anti-Mpl and parental anti-HER3 IgG bound only to their corresponding cognate antigen (FIG. 6).

D. Antibodies Containing an Engineered Fc Region are Capable of Efficient Antibody-Dependent Cell-Mediated Cytotoxicity.

To demonstrate that the engineered $F_c$ region ($C_H3$ mutations, supra) utilized in generating the exemplified bispecific antibodies of the invention is capable of efficient antibody-dependent cell-mediated cytotoxicity (ADCC), the following experiment was performed.

The $C_H3$ mutations maintain the ability to support efficient antibody-dependent cell-mediated cytotoxicity (ADCC) as demonstrated using the method of Lewis, G. D. et al. (Lewis, G. D, et al. (1993) Cancer Immunol. Immunother. 37:255-263, hereby incorporated by reference in its entirety). Briefly, cytotoxicity assays were performed with $^{51}$Cr-labeled SK-BR-3 and HBL-100 target cells (ATCC accession numbers HTB-30 and 45509, respectively) and human peripheral blood lymphocytes as effector cells. However, unlike Lewis et al., the lymphocytes were not activated with IL-2.

Figure 7:
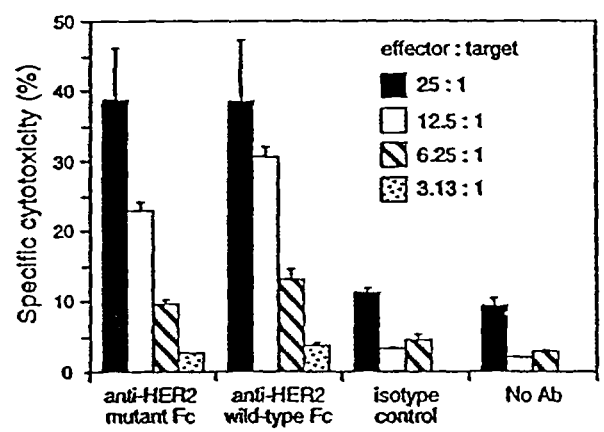
FIG. 7 is a bar graph of the results of an antibody-dependent cell-mediated cytotoxicity (ADCC) study. ADCC was mediated by huMAb4D5-5 (Carter, P. et al. (1992) PNAS USA 89:4285-4289) containing either a mutant (S354C: T366W/Y349'C:T366'S:L368'A:Y407'V) or wild-type Fc or an isotype-matched control antibody (E25, Presta, L. G. et al. (1993) J. Immunol. 151:2623-2632). The antibodies (125 ng/ml) were incubated with human peripheral blood mononuclear effector cells and SK-BR-3 target cells at the ratios shown. Data presented are the mean of triplicate measurements and representative of three separate experiments.

The $C_H3$ mutations S354:T366W and Y349:T366S: L368A:Y407V were introduced separately into the H chain of the humanized anti-HER2 antibody, huMAb4D5-5 prepared by Carter et al. (Carter, P. et al. (1992) PNAS USA 89:4285-4289). Antibodies containing remodeled and wild-type Fc regions had similar potency in ADCC with the HER2-overexpressing breast cancer cell line, SK-BR-3 (FIG. 7). Both remodeled and wild-type antibodies showed comparable, low activity against the normal breast epithelial cell line. The effects in the H-chain are independent of the binding domains, predicting that these BsIgG's will function in antibody-dependent cell-mediated cytotoxicity.

The instant invention is shown and described herein in what is considered to be the most practical, and the preferred embodiments. It is recognized, however, that departures may be made therefrom which are within the scope of the invention, and that obvious modifications will occur to one skilled in the art upon reading this disclosure. All references provided herein are herein incorporated by reference in their entirety.

The invention claimed is:

1. A method of measuring the formation of a heteromeric multispecific antibody from a mixture of polypeptides, wherein the heteromeric multispecific antibody comprises four polypeptides, wherein the first polypeptide and the second polypeptide of the four polypeptides each comprise a heavy chain constant domain and a heavy chain variable domain, and the third polypeptide and the fourth polypeptide of the four polypeptides are each common light chains that are identical to each other;
  wherein the first polypeptide and the third polypeptide form a binding domain that binds a first antigen, and wherein the second polypeptide and the fourth polypeptide form a binding domain that binds a different antigen;
  wherein the first polypeptide and the second polypeptide each further comprise a multimerization domain,
  wherein the multimerization domain of either the first polypeptide or the second polypeptide, or of both the first polypeptide and the second polypeptide, is altered by amino-acid substitution to form a non-naturally occurring disulfide bond between a free thiol-containing residue in the multimerization domain of the first polypeptide and a free thiol-containing residue in the multimerization domain of the second polypeptide;
  wherein the first and second polypeptides dimerize by interaction of the first and second multimerization domains to form the heteromeric multispecific antibody;
the method comprising the steps of:
  (i) causing the mixture of polypeptides from which the heteromeric multispecific antibody is formed to migrate in a gel matrix, and
  (ii) determining the relative amount of a migrating band corresponding to the heteromeric multispecific antibody having a non-naturally occurring disulfide bond between the first and second polypeptides, and a slower migrating band corresponding to a heteromultimer lacking a non-naturally occurring disulfide bond between the first and second polypeptide.

2. The method of claim 1, wherein the multimerization domains further comprise a protuberance-into-cavity interaction between the first and second polypeptides.

3. The method of claim 2, wherein the method further comprises before step (i):
  expressing from a first nucleic acid the first polypeptide, wherein the first nucleic acid is altered to encode an amino acid residue having a larger side chain volume, thereby generating a protuberance on the first polypeptide multimerization domain, and
  expressing from a second nucleic acid the second polypeptide, wherein the second nucleic acid is altered to encode an amino acid residue having a smaller side chain volume, thereby generating a cavity on the second polypeptide multimerization domain wherein the protuberance is positioned to interact with the cavity.

4. The method of claim 3, wherein the step of altering the first or the second nucleic acid to generate a protuberance or generating a cavity, or both, occurs by phage display selection.

5. The method of claim 3, wherein the amino acid residue having a larger side chain volume than the substituted amino acid is selected from the group consisting of arginine (R), phenylalanine (F), tyrosine (Y), tryptophan (W), isoleucine (I) and leucine (L).

6. The method of claim 3 wherein the amino acid residue having a smaller side chain volume than the substituted amino acid is selected from the group consisting of glycine (G), alanine (A), serine (S), threonine (T), and valine (V), and wherein the import residue is not cysteine (C).

7. The method of claim 1, wherein the multimerization domain is at least a part of a $C_H3$ domain region of an antibody constant domain, and the non-naturally occurring disulfide bond is between the $C_H3$ multimerization domains of the first and second polypeptides.

8. The method of claim 1, wherein the heavy chain constant domain is the heavy chain constant domain of an IgG.

9. The method of claim 8 wherein the IgG is a human IgG.

10. The method of claim 1, wherein the heavy chain constant domain is a $C_H3$ domain.

11. The method of claim 10 wherein the $C_H3$ domain is a human $C_H3$ domain.

* * * * *